US012590125B2

(12) United States Patent
Neogi et al.

(10) Patent No.: US 12,590,125 B2
(45) Date of Patent: Mar. 31, 2026

(54) PEPTIDE INHIBITORS FOR THE INHIBITION OF HIV CAPSID

(71) Applicants: THE CURATORS OF THE UNIVERSITY OF MISSOURI, Columbia, MO (US); Ujjwal Neogi, Stockholm (SE); Anders Sonnerborg, Stockholm (SE)

(72) Inventors: Ujjwal Neogi, Stockholm (SE); Anders Sonnerborg, Stockholm (SE); Kamlendra Singh, Columbia, MO (US); Thomas P. Quinn, Columbia, MO (US); Fabio Gallazzi, Columbia, MO (US)

(73) Assignee: THE CURATORS OF THE UNIVERSITY OF MISSOURI, Columbia, MO (US)

( * ) Notice: Subject to any disclaimer, the term of this patent is extended or adjusted under 35 U.S.C. 154(b) by 851 days.

(21) Appl. No.: 17/616,877

(22) PCT Filed: Jun. 8, 2020

(86) PCT No.: PCT/US2020/036658
    § 371 (c)(1),
    (2) Date: Dec. 6, 2021

(87) PCT Pub. No.: WO2020/247933
    PCT Pub. Date: Dec. 10, 2020

(65) Prior Publication Data
    US 2022/0306690 A1      Sep. 29, 2022

Related U.S. Application Data

(60) Provisional application No. 62/858,666, filed on Jun. 7, 2019.

(51) Int. Cl.
    *C07K 7/08*      (2006.01)
    *A61K 38/00*     (2006.01)
    *A61P 31/18*     (2006.01)
    *C07K 7/64*      (2006.01)

(52) U.S. Cl.
    CPC .............. *C07K 7/08* (2013.01); *A61P 31/18* (2018.01); *C07K 7/64* (2013.01); *A61K 38/00* (2013.01)

(58) Field of Classification Search
    None
    See application file for complete search history.

(56) References Cited

U.S. PATENT DOCUMENTS

2007/0032636 A1    2/2007    Sakalian et al.
2019/0038704 A1    2/2019    Pasquale et al.

FOREIGN PATENT DOCUMENTS

| JP | 2011522796 A | 8/2011 |
|---|---|---|
| KR | 20030082191 A | 10/2003 |
| RU | 2603732 C2 | 11/2016 |
| WO | 2006056468 A1 | 6/2006 |
| WO | 2009137532 A1 | 11/2009 |
| WO | 2012113921 A1 | 8/2012 |
| WO | 2014016358 A1 | 1/2014 |
| WO | 2014093702 A1 | 6/2014 |
| WO | 2018053013 A1 | 3/2018 |
| WO | 2018085836 A1 | 5/2018 |

OTHER PUBLICATIONS

GenBank Accession No. AAF99754.1, 2 pages (2001) (Year: 2001).*
CAPLUS Abstract of Jeong et al., Nucl. Acids Res. 33:7066-7073 (2005), Accession No. 2006:25696, 2 pages (2006) (Year: 2006).*
Jeong et al., Nucl. Acids Res. 33:7066-7073 (2005) (Year: 2005).*
Betts et al., "Chapter 14: Amino Acid Properties and Consequences of Substitutions," Bioinformatics for Geneticists, eds., Barnes et al., John Wiley & Dons, Ltd., p. 289-316 (2003) (Year: 2003).*
Butterfield et al., Biochem. 49:1549-1555 (2010) with supplemental information (Year: 2010).*
Teeraananchai et al., "Life expectancy of HIV-positive people after starting combination antiretroviral therapy: a meta-analysis", HIV Medicine, 2017, pp. 256-266, vol. 18.
Ternois et al., "The HIV-1 capsid protein C-terminal domain in complex with a virus assembly inhibitor", Nature Structural & Molecular Biology, Aug. 2005, pp. 678-682, vol. 12, No. 8.
Thenin-Houssier et al., "Ebselen, a Small-Molecule Capsid Inhibitor of HIV-1 Replication", Antimicrobial Agents and Chemotherapy, Apr. 2016, pp. 2195-2208, vol. 60, No. 4.
Tremblay et al., "Inhibition of HIV-1 capsid assembly: Optimization of the antiviral potency by site selective modifications at N1, C2 and C16 of a 5-(5-furan-2-yl-pyrazol-1-yl)-1H-benzimidazole scaffold", Bioorganic & Medicinal Chemistry Letters, 2012, pp. 7512-7517, vol. 22.
Tse et al., "Discovery of Novel Potent HIV Capsid Inhibitors with Long-Acting Potential", Feb. 14-17, 2017, Seattle WA, 9 pages.
Vozzolo et al., "Gyrase B Inhibitor Impairs HIV-1 Replication by Targeting Hsp90 and the Capsid Protein", The Journal of Biological Chemistry, Dec. 2010, pp. 39314-39328, vol. 285, No. 50.
Zhang et al., "Dual-acting stapled peptides target both HIV-1 entry and assembly", Retrovirology, 2013, 20 pages, vol. 10, No. 136.
Zheng et al., "539. GS-CA2: A Novel, Potent, and Selective First-In-class Inhibitor of HIV-1 Capsid Function Displays Nonclinical Pharmacokinetics Supporting Long-Acting Potential in Humans", Open Forum Infectious Diseases, 2018, pp. 199-200, vol. 5, No. Suppl. 1.
Zhou et al., "HIV-1 Resistance to the Capsid-Targeting Inhibitor PF74 Results in Altered Dependence on Host Factors Required for Virus Nuclear Entry", Journal of Virology, Sep. 2015, pp. 9068-9079, vol. 89, No. 17.

(Continued)

*Primary Examiner* — Thea D'Ambrosio
(74) *Attorney, Agent, or Firm* — Thompson Coburn LLP; William A. J. Holtz D.

(57) ABSTRACT

Provide for herein are cyclic or linear peptides that bind HIV-1 capsid protein and inhibit HIV-1 capsid from assembling and/or disassembling. Further provided are methods of making said peptides and pharmaceutical compositions and methods for treating HIV infection.

25 Claims, 11 Drawing Sheets

Figure 1A:
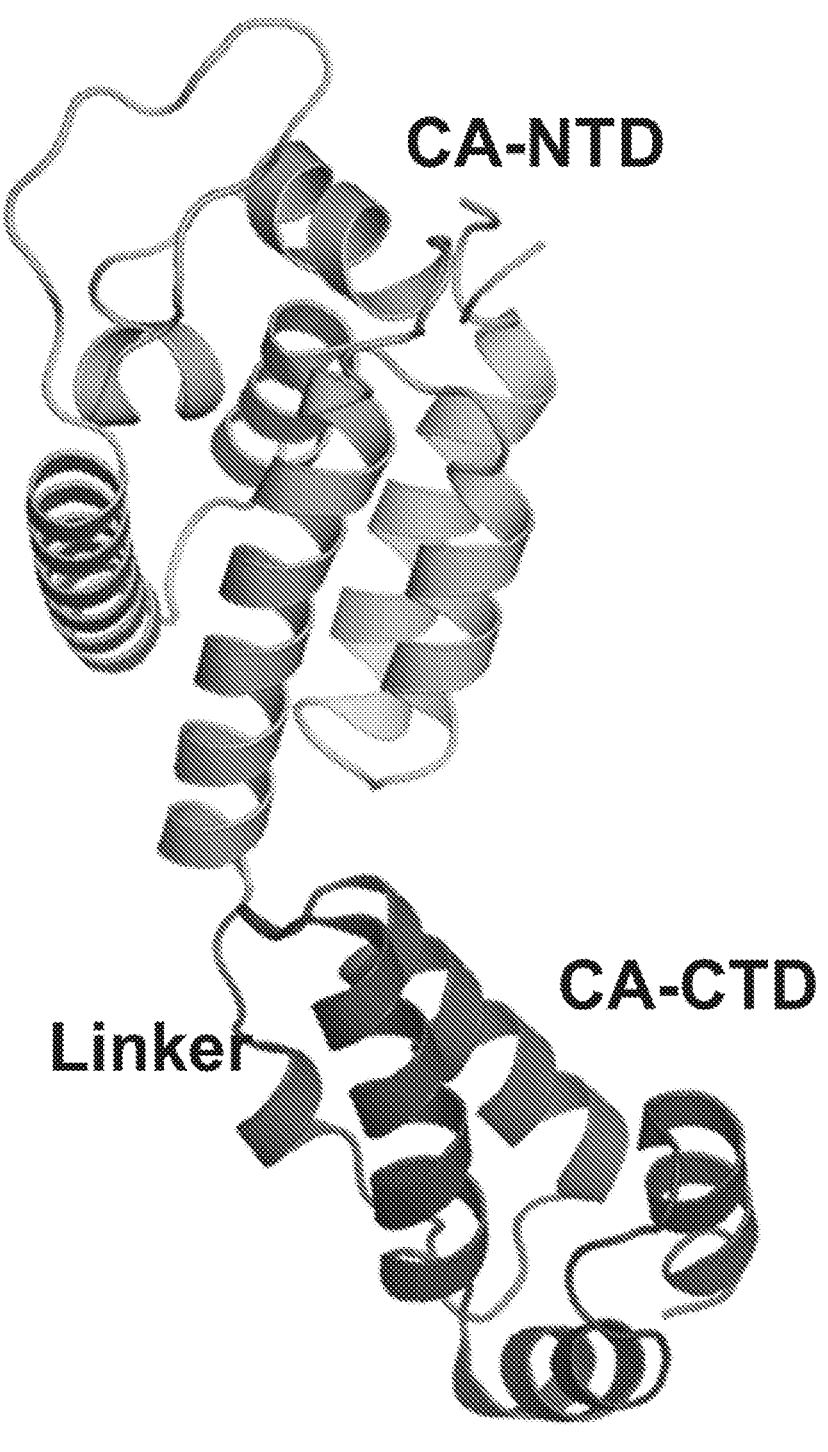

Specification includes a Sequence Listing.

(56) References Cited

OTHER PUBLICATIONS

Acevedo et al., "Identification of HIV Inhibitors Guided by Free Energy Perturbation Calculations", Current Pharmaceutical Design, 2012, pp. 1199-1216; vol. 18, No. 9.

Ambrose et al., "HIV-1 Uncoating: Connection to Nuclear Entry and Regulation by Host Proteins", Virology, 2014, pp. 371-379.

Antiretroviral Therapy Cohort Collaboration, "Survival of HIV-positive patients starting antiretroviral therapy between 1996 and 2013: a collaborative analysis of cohort studies", Lancet HIV, 2017, pp. e349-e356, vol. 4.

Bhattacharya et al., "Structural basis of HIV-1 capsid recognition by PF74 and CPSF6", Proceedings of the National Academy of Sciences, 2014, pp. 18625-18630, vol. 111, No. 52.

Bichel et al., "HIV-1 capsid undergoes coupled binding and isomerization by the nuclear pore protein NUP358", Retrovirology, 2013, 12 pages, vol. 10, No. 81.

Blair et al., "HIV Capsid is a Tractable Target for Small Molecule Therapeutic Intervention", PLOS Pathogens, 2010, 10 pages, vol. 6, No. 12.

Bocanegra et al., "Molecular recognition in the human immunodeficiency virus capsid and antiviral design", Virus Research, 2012, pp. 388-410, vol. 169.

Campbell et al., "HIV-1 Capsid: The Multifaceted Key Player in HIV-1 infection", Nature Reviews Microbiology, 2015, pp. 471-483, vol. 13, No. 8.

Carnes et al., "Inhibitors of the HIV-1 Capsid, A Target of Opportunity", Current Opinion in HIV and AIDS, Jul. 2018, pp. 359-365, vol. 13, No. 4.

Chen et al., "HIV-1 capsid is involved in post-nuclear entry steps", Retrovirology, 2016, 16 pages, vol. 13.

Curreli et al., "Virtual screening based identification of novel small-molecule inhibitors targeted to the HIV-1 capsid", Bioorganic & Medicinal Chemistry, Jan. 2011, pp. 77-90, vol. 19.

Fader et al., "Discovery of a 1,5-dihydrobenzo[b][1,4]diazepine-2,4-dione series of inhibitors of HIV-1 capsid assembly", Bioorganic & Medicinal Chemistry Letters, 2011, pp. 398-404, vol. 21.

Forshey et al., "Formation of a Human Immunodeficiency Virus Type 1 Core of Optimal Stability Is Crucial for Viral Replication", Journal of Virology, Jun. 2002, pp. 5667-5677, vol. 76, No. 11.

Francis et al., "Single HIV-1 imaging reveals progression of infection through CA-dependent steps of docking at the nuclear pore, uncoating and nuclear transport", Cell Host & Microbe, Apr. 2018, pp. 536-548, vol. 23, No. 4.

Fricke et al., "BI-2 destabilizes HIV-1 cores during infection and Prevents Binding of CPSF6 to the HIV-1 Capsid", Retrovirology, 2014, 7 pages, vol. 11.

Gamble et al., "Crystal Structure of Human Cyclophilin A Bound to the Amino-Terminal Domain of HIV-1 Capsid", Cell, Dec. 1996, pp. 1285-1294, vol. 87.

Genheden et al., "How to Obtain Statistically Converged MM/GBSA Results", Journal of Computational Chemistry, 2010, pp. 837-846, vol. 31, No. 4.

Gres et al., "X-Ray Structures of Native HIV-1 Capsid Protein Reveal Conformational Variability", Science, Jul. 2015, pp. 99-103, vol. 349.

Harries et al., "Ending the HIV/AIDS epidemic in low- and middle-income countries by 2030: is it possible?", F1000Research, 2016, 8 pages, vol. 5.

Jarvis, "Conquering HIV's capsid", Chemical & Engineering News, Jul. 2017, 5 pages, vol. 95, No. 31.

Jerabek-Willemsen et al., "MicroScale Thermophoresis: Interaction analysis and beyond", Journal of Molecular Structure, 2014, pp. 101-113, vol. 1077.

Karlin et al., "Applications and statistics for multiple high-scoring segments in molecular sequences", Proceedings of the National Academy of Sciences, Jun. 1993, pp. 5873-5877, vol. 90.

Kelly et al., "Structure of the antiviral assembly inhibitor CAP-1 bound to the HIV-1 CA protein", Journal of Molecular Biology, Oct. 2007, pp. 355-366, vol. 373, No. 2.

Kortagere et al., "Inhibiting Early-Stage Events in HIV-1 Replication by Small-Molecule Targeting of the HIV-1 Capsid", Journal of Virology, Aug. 2012, pp. 8472-8481, vol. 86, No. 16.

Kortagere et al., "Structure-Activity Relationships of a Novel Capsid Targeted Inhibitor of HIV-1 Replication", Journal of Chemical Information, 2014, pp. 3080-3090, vol. 54.

Krishnan et al., "Structure-based modeling of the functional HIV-1 intasome and its inhibition", Proceedings of the National Academy of Sciences, Sep. 2010, pp. 15910-15915, vol. 107, No. 36.

Lamorte et al., "Discovery of Novel Small-Molecule HIV-1 Replication Inhibitors That Stabilize Capsid Complexes". Antimicrobial Agents and Chemotherapy, Oct. 2013, pp. 4622-4631, vol. 57, No. 10.

Lee et al., "Flexible use of nuclear import pathways by HIV-1", Cell Host & Microbe, Mar. 2010, pp. 221-233, vol. 7, No. 3.

Lemke et al., "A novel inhibitor-binding site on the HIV-1 capsid N-terminal domain leads to improved crystallization via compound-mediated dimerization", Acta Crystallographica Section D Biological Crystallography, 2013, pp. 1115-1123, vol. 69.

Lemke et al., "Distinct Effects of Two HIV-1 Capsid Assembly Inhibitor Families That Bind the Same Site within the N-Terminal Domain of the Viral CA Protein", Journal of Virology, Jun. 2012, pp. 6643-6655, vol. 86, No. 12.

Li et al., "Functional conservation of HIV-1 Gag: implications for rational drug design", Retrovirology, 2013, vol. 10, No. 126.

Matreyek et al., "Nucleoporin NUP153 Phenylalanine-Glycine Motifs Engage a Common Binding Pocket within the HIV-1 Capsid Protein to Mediate Lentiviral Infectivity", PLOS Pathogens, Oct. 2013, 21 pages, vol. 9, No. 10.

May et al., "Impact on life expectancy of HIV-1 positive individuals of CD4R cell count and viral load response to antiretroviral therapy", AIDS, 2014, pp. 1193-1202, vol. 28, No. 8.

NCBI Reference Sequence Entry: WP_071864822.1, "FtsW/RodA/SpoVE family cell cycle protein [Enterococcus canintestini]", 2017, retrieved from https://www.ncbi.nlm.nih.gov/protein/WP_071864822.1 on Sep. 4, 2020.

NCBI Reference Sequence entry: WP_090225036.1 "GLPGLI family protein [Lutibacter maritimus]", 2017, retrieved from https://www.ncbi.nim.nih.gov/protein/WP_090225036 on Sep. 4, 2020.

Perrier et al., "Prevalence of gag mutations associated with in vitro resistance to capsid inhibitor GS-CA1 in HIV-1 antiretroviral-naive patients", Journal of Antimicrobial Chemotherapy, 2017, pp. 2954-2955, vol. 72.

Pornillos et al., "Atomic level modeling of the HIV capsid", Nature, Jan. 2011, pp. 424-427, vol. 469, No. 7330.

Pornillos et al., "X-ray Structures of the Hexameric Building Block of the HIV Capsid", Cell, Jun. 2009, pp. 1282-1292, vol. 137, No. 7.

Prevelige Jr., "New Approaches for Antiviral Targeting of HIV Assembly", Journal of Molecular Biology, Jul. 2011, pp. 634-640, vol. 410, No. 4.

Price et al., "CPSF6 Defines a Conserved Capsid Interface that Modulates HIV-1 Replication", PLOS Pathogens, Aug. 2012, 14 pages, vol. 8 , No. 8.

Price et al., "Host Cofactors and Pharmacologic Ligands Share an Essential Interface in HIV-1 Capsid That Is Lost upon Disassembly", PLOS Pathogens, 17 pages, Oct. 2014, vol. 10, No. 10.

Quinn, "HIV epidemiology and the effects of antiviral therapy on long-term consequences", AIDS, Sep. 2008, pp. S7-S12, vol. 22, No. Suppl. 3.

Sabin, "Do people with HIV infection have a normal life expectancy in the era of combination antiretroviral therapy?", BMC Medicine, Nov. 2013, 7 pages, vol. 11, No. 251.

Sager et al., "Safety and PK of Subcutaneous GS-6207, a Novel HIV-1 Capsid Inhibitor", Conference on Retroviruses and Opportunistic Infections, Mar. 4-7, 2019, Seattle, Washington, 8 pages.

Schaller et al., "HIV-1 Capsid-Cyclophilin Interactions Determine Nuclear Import Pathway, Integration Targeting and Replication Efficiency", PLoS Pathogens, Dec. 2011, 15 pages, vol. 7, No. 12.

Schneidman-Duhovny et al., "PatchDock and SymmDock: servers for rigid and symmetric docking", Nucleic Acids Research, 2005, pp. W363-W367, vol. 33.

(56) References Cited

OTHER PUBLICATIONS

Shi et al., "Compensatory Substitutions in the HIV-1 Capsid Reduce the Fitness Cost Associated with Resistance to a Capsid-Targeting Small-Molecule Inhibitor", Journal of Virology, Jan. 2015, pp. 208-219, vol. 89, No. 1.

Shi et al., "Small-Molecule Inhibition of Human Immunodeficiency Virus Type 1 Infection by Virus Capsid Destabilization", Journal of Virology, Jan. 2011, pp. 542-549, vol. 85, No. 1.

Sticht et al., "A Peptide Inhibitor of HIV-1 Assembly In Vitro", Aug. 2005, Nature Structural & Molecular Biology, pp. 671-677, vol. 12, No. 8.

Tang et al., "Antiviral Inhibition of the HIV-1 Capsid Protein", Journal of Molecular Biology, 2003, pp. 1013-1020, vol. 327.

"Accessory colonization factor AcfA-like protein [Aliivibrio fischeri ES114]", : Database GenPept (online), Accesion No. AAW86473, Mar. 2017, 2 pages, https://www.ncbi.nlm.nih.gov/protein/59480686?sat=4&satkey=190601709.

Muppidi et al., "Design of antiviral stapled peptides containing a biphenyl cross-linker", Bioorganic Medicinal Chemistry Letters, 2014, pp. 1748-1751, vol. 24, No. 7.

Dewan, "Cyclic Peptide Inhibitors of HIV-1 Capsid-Human lysyl-tRNA Synthetase Interaction", 2012, ACS Chemical Biology, pp. 761-769, vol. 7, No. 4.

Chen et al., "Generation and Analysis of Random Point Mutations in an Antibody CDR2 Sequence: Many Mutated Antibodies Lose Their Ability to Bind Antigen", Journal of Experimental Medicine, Sep. 1992, pp. 855-866, vol. 176.

Pakula et al., "Genetic Analysis of Protein Stability and Function", Annual Review of Genetics, 1989, pp. 289-310, vol. 23.

Rudikoff, et al., "Single amino acid substitution altering antigen-binding specificity", Proceedings of the National Academy of Sciences of the United States of America, Mar. 1982, pp. 1979-1983, vol. 79.

Singer et al., "Genes and Genomes", 1998, 4 pages, vol. 1, translated from English, Moscow "Mir".

\* cited by examiner

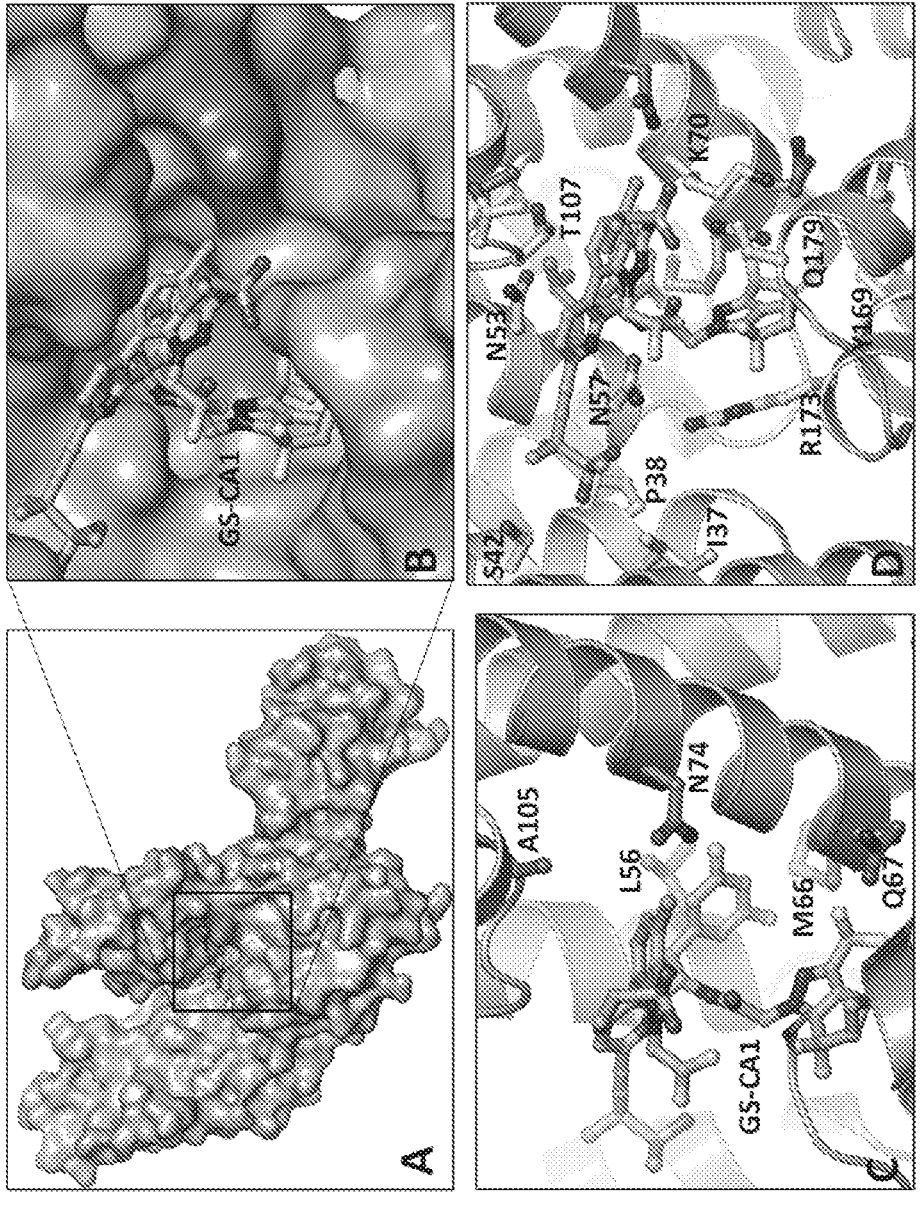
Figure 2A,B,C,D

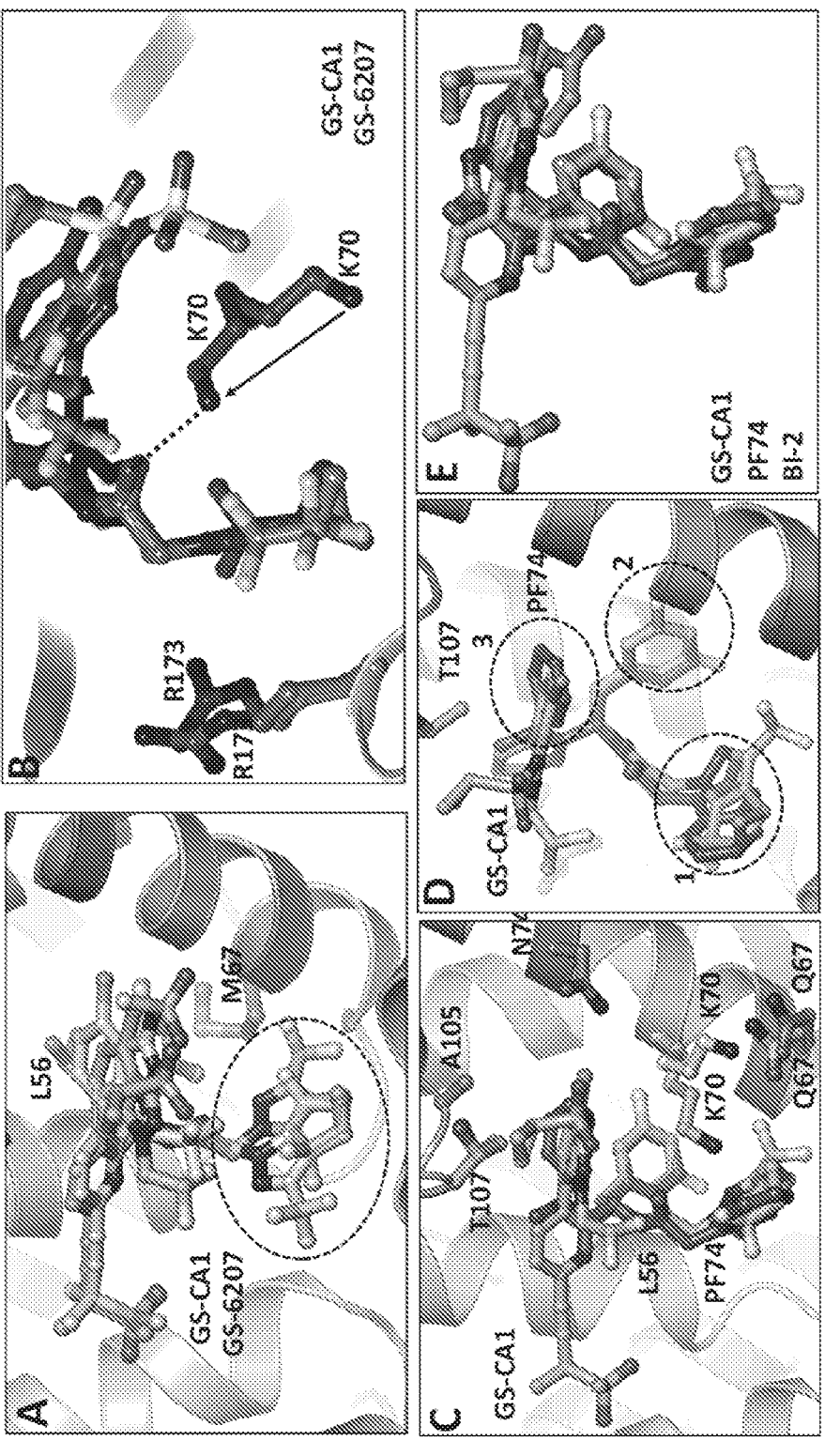
Figure 3A,B,C,D,E

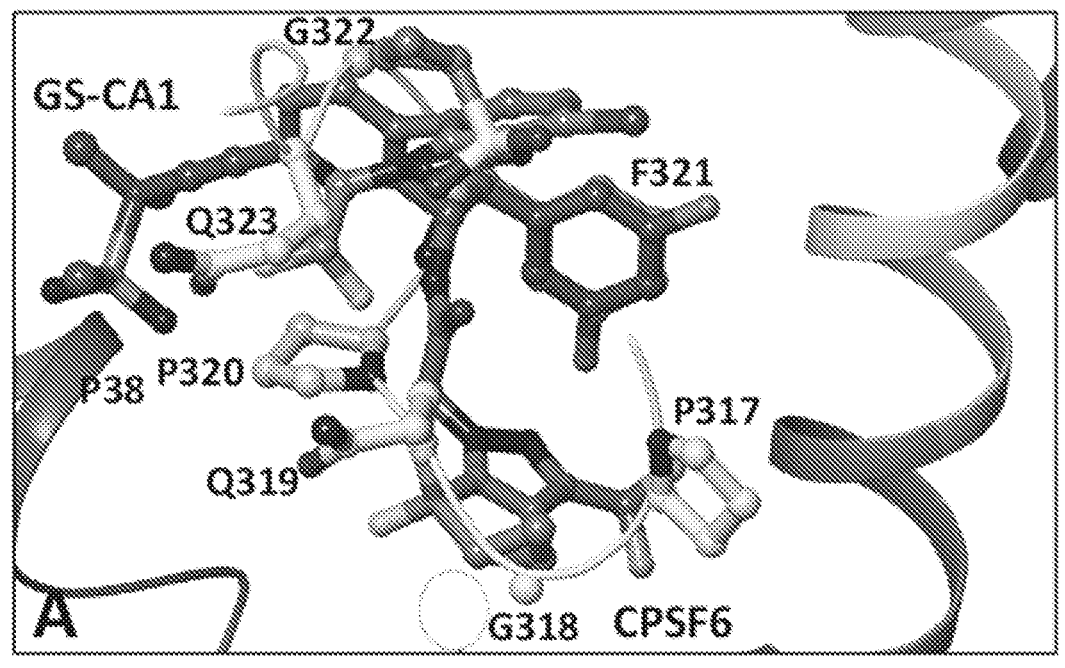
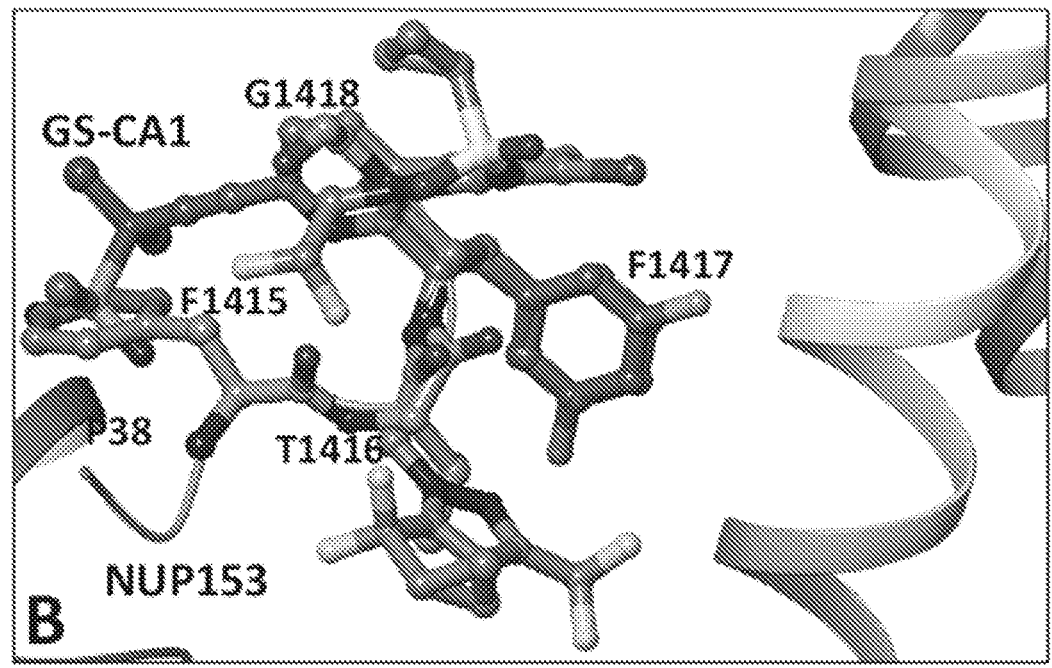
Figure 4A,B

Figure 6A,B $$EC_{50} = 0.96 \ \mu M$$

| SEQ ID NO: | Sequence | name | MW |
|---|---|---|---|
| 4 | cyc(SGVFTFGPVNFPG) | Pep-2-cyclic | 1306.6 |
| 4 | h2n-SGVFTFGPVNFPG-conh2 | Pep-2-linear | 1323.6 |
| 6 | h2n-PVLFPGQPFGQPPL-conh2 | CPSF6 | 1492.7 |
| 5 | cyc(SGVFYFWPVNFPG) | Pep-3-cyclic | 1497.7 |
| 5 | h2n-SGVFYFWPVNFPG-cooh | Pep-3-linear | 1515.7 |

Figure 10

SEQUENCE LISTING

```
<160> NUMBER OF SEQ ID NOS: 6

<210> SEQ ID NO 1
<211> LENGTH: 230
<212> TYPE: PRT
<213> ORGANISM: Homo sapiens

<400> SEQUENCE: 1

Pro Ile Val Gln Asn Leu Gln Gly Gln Met Val His Gln Ala Ile Ser
1               5                   10                  15

Pro Arg Thr Leu Asn Ala Trp Val Lys Val Ile Glu Glu Lys Ala Phe
            20                  25                  30

Ser Pro Glu Val Ile Pro Met Phe Thr Ala Leu Ser Glu Gly Ala Thr
        35                  40                  45

Pro Gln Asp Leu Asn Thr Met Leu Asn Thr Val Gly Gly His Gln Ala
    50                  55                  60

Ala Met Gln Met Leu Lys Asp Thr Ile Asn Glu Glu Ala Ala Glu Trp
65                  70                  75                  80

Asp Arg Leu His Pro Val His Ala Gly Pro Ile Ala Pro Gly Gln Met
            85                  90                  95

Arg Glu Pro Arg Gly Ser Asp Ile Ala Gly Thr Thr Ser Thr Leu Gln
            100                 105                 110

Glu Gln Ile Ala Trp Met Thr Ser Asn Pro Pro Ile Pro Val Gly Asp
        115                 120                 125

Ile Tyr Lys Arg Trp Ile Ile Leu Gly Leu Asn Lys Ile Val Arg Met
    130                 135                 140

Tyr Ser Pro Val Ser Ile Leu Asp Ile Lys Gln Gly Pro Lys Glu Pro
145                 150                 155                 160

Phe Arg Asp Tyr Val Asp Arg Phe Phe Lys Thr Leu Arg Ala Glu Gln
                165                 170                 175

Ala Thr Gln Asp Val Lys Asn Trp Met Thr Asp Thr Leu Leu Val Gln
            180                 185                 190

Asn Ala Asn Pro Asp Cys Lys Thr Ile Leu Arg Ala Leu Gly Pro Gly
            195                 200                 205

Ala Thr Leu Glu Glu Met Thr Ala Cys Gln Gly Val Gly Gly Pro Ser
    210                 215                 220

His Lys Ala Arg Val Leu
```

225                    230

<210> SEQ ID NO 2
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa is glycine (G), lysine (K), or a polar
      uncharged amino acid.
<220> FEATURE:
<221> NAME/KEY: MISC_FEATURE
<222> LOCATION: (4)..(4)
<223> OTHER INFORMATION: Xaa is glycine (G), lysine (K), or a polar
      uncharged amino acid.
<220> FEATURE:
<221> NAME/KEY: MISC_FEATURE
<222> LOCATION: (7)..(7)
<223> OTHER INFORMATION: Xaa is glycine (G), lysine (K), or a polar
      uncharged amino acid.

<400> SEQUENCE: 2

Phe Xaa Phe Xaa Pro Val Xaa Phe
1               5

<210> SEQ ID NO 3
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is glycine (G), proline (P), lysine (K), a
      polar uncharged amino acid, or a hydrophobic amino acid.
<220> FEATURE:
<221> NAME/KEY: MISC_FEATURE
<222> LOCATION: (2)..(2)
<223> OTHER INFORMATION: Xaa is glycine (G), proline (P), lysine (K), a
      polar uncharged amino acid, or a hydrophobic amino acid.
<220> FEATURE:
<221> NAME/KEY: MISC_FEATURE
<222> LOCATION: (3)..(3)
<223> OTHER INFORMATION: Xaa is glycine (G), proline (P), lysine (K), a
      polar uncharged amino acid, or a hydrophobic amino acid.
<220> FEATURE:
<221> NAME/KEY: MISC_FEATURE
<222> LOCATION: (5)..(5)
<223> OTHER INFORMATION: Xaa is glycine (G), lysine (K), or a polar
      uncharged amino acid.
<220> FEATURE:
<221> NAME/KEY: MISC_FEATURE
<222> LOCATION: (7)..(7)
<223> OTHER INFORMATION: Xaa is glycine (G), lysine (K), or a polar
      uncharged amino acid.
<220> FEATURE:
<221> NAME/KEY: MISC_FEATURE
<222> LOCATION: (10)..(10)
<223> OTHER INFORMATION: Xaa is glycine (G), lysine (K), or a polar
      uncharged amino acid.
<220> FEATURE:
<221> NAME/KEY: MISC_FEATURE
<222> LOCATION: (12)..(12)
<223> OTHER INFORMATION: Xaa is glycine (G), proline (P), lysine (K), a
      polar uncharged amino acid, or a hydrophobic amino acid.
<220> FEATURE:
<221> NAME/KEY: MISC_FEATURE
<222> LOCATION: (13)..(13)
<223> OTHER INFORMATION: Xaa is glycine (G), proline (P), lysine (K), a
      polar uncharged amino acid, or a hydrophobic amino acid.

<400> SEQUENCE: 3

-continued

```
Xaa Xaa Xaa Phe Xaa Phe Xaa Pro Val Xaa Phe Xaa Xaa
1               5               10

<210> SEQ ID NO 4
<211> LENGTH: 13
<212> TYPE: PRT
<213> ORGANISM: Artificial Sequence
<220> FEATURE:
<223> OTHER INFORMATION: Synthetic

<400> SEQUENCE: 4

Ser Gly Val Phe Thr Phe Gly Pro Val Asn Phe Pro Gly
1               5               10

<210> SEQ ID NO 5
<211> LENGTH: 13
<212> TYPE: PRT
<213> ORGANISM: Artificial Sequence
<220> FEATURE:
<223> OTHER INFORMATION: Synthetic

<400> SEQUENCE: 5

Ser Gly Val Phe Tyr Phe Trp Pro Val Asn Phe Pro Gly
1               5               10

<210> SEQ ID NO 6
<211> LENGTH: 14
<212> TYPE: PRT
<213> ORGANISM: Artificial Sequence
<220> FEATURE:
<223> OTHER INFORMATION: Synthetic

<400> SEQUENCE: 6

Pro Val Leu Phe Pro Gly Gln Pro Phe Gly Gln Pro Pro Leu
1               5               10
```

PEPTIDE INHIBITORS FOR THE INHIBITION OF HIV CAPSID

CROSS-REFERENCE TO RELATED APPLICATIONS

This is a U.S. National Phase application of PCT application PCT/US2020/036658, filed on Jun. 8, 2020, which claims the benefit of U.S. provisional application 62/858,666, filed Jun. 7, 2019, each of which are incorporated herein by reference in their entireties.

REFERENCE TO SEQUENCE LISTING SUBMITTED ELECTRONICALLY

The content of the electronically submitted sequence listing in ASCII text file (Name UMC_196127_Seq_List_ST25.txt; Size: 5026 bytes; and Date of Creation: Jun. 8, 2020) filed with the application is incorporated herein by reference in its entirety.

BACKGROUND

Exceptional developments in combination antiretroviral therapy (cART) have transformed HIV/AIDS from a deadly pandemic to a chronic and manageable disease (Antiviral Therapy Cohort, 2017). If administered efficiently, cART significantly reduces morbidity and mortality of HIV infected individuals, both in resource-rich and in low- and middle-income countries (Quinn, 2008; Sabin, 2013; May et al. 2014, Harries et al. 2016; and Teeraanachai et al., 2017). However, emerging drug resistance mutations (DRMs) continue to threaten the desired outcome of cART.

HIV-capsid (CA) has emerged as a significant potential antiviral target over the past 15 years due to increased understanding of its involvement in the viral life cycle. The CA protein has two distinct domains, an N-terminal domain (CA-NTD) and a C-terminal domain (CA-CTD), which are connected by a flexible linker of ~5 amino acid residues (FIG. 1A). Both the CA-NTD and the CA-CTD domains contain mostly $\alpha$-helical secondary structure. The CA-NTD is composed of seven $\alpha$-helices ($\alpha1$-$\alpha7$), whereas CA-CTD consists of four $\alpha$-helices ($\alpha8$-$\alpha11$) and a short $3_{10}$-helix. The structures of CA have revealed interactions between CA promoters in the form of hexameric and pentameric building blocks (Pornillos et al., 2009; and Pornillos et al., 2011). These structures also revealed that the fullerene-like structure of the capsid core is composed of 1,500 copies of CA organized into a lattice of ~250 hexamers and 12 pentamers that facilitate closure of the capsid core.

The capsid core is involved in multiple steps of HIV replication. Following infection and fusion of viral and cellular membranes, the capsid core enters the cytosol where it undergoes controlled disassembly, process known as uncoating, as it moves through the cytosol to dock at the nuclear pore. The timing, process, and extent of uncoating the capsid core in the cytosol is not entirely known, but it has been suggested that uncoating is associated with the initiation of reverse transcription (Campbell and Hope, 2015). Once the capsid core reaches the nuclear pore, CA facilitates nuclear entry and enters the nucleus along with the preintegration complex. CA may also be involved in the integration of viral DNA into the host chromosome, but the specific role of CA in this process has not been well defined (Schaller et al., 2011; Chen et al., 2016; and Francis and Melikyan, 2018). During vial assembly (late stage of viral replication), the Gag polyprotein, which is the precursor of the capsid protein, assembles at the plasma membrane and buds as a spherical, immature non-infectious virus. Upon activation of the viral protease during maturation, Gag is processed into several structural proteins and small peptides, including the multifunctional CA (FIG. 1A), forming a conical capsid core (also referred to as capsid or core). Thus, CA plays an important role in HIV biology.

Many reports have shown that the stability of the capsid core and its interaction with host factors influences reverse transcription. Mutations that alter lattice stability or interactions between CA building blocks alter replication events and can severely impact viral infectivity. For example, stabilizing mutations E45A and E128A/R132A or destabilizing mutations R18A/N21A, P38A, Q63A, L136D, K170A, and Q129A that lead to either slow or rapid uncoating, respectively, ultimately decrease viral infectivity (Forshey et al, 2002). While destabilization must occur for successful replication, balance between stabilization and dissociation must be maintained, demonstrating an intricate link between capsid and viral infectivity. Similarly, disruption of CA interactions with a variety of host factors, including CPSF6 (cleavage and polyadenylation specific factor 6, TNPO3 (transportin 3), NUP153 (nucleoporin 153), NUP 358 (nucleoporin 358), and Cyclophilin A, has been shown to impact infectivity during replication (Krishnan et al. 2010; Lee et al. 2010; Schaller et al., 2011; Ambrose et al., 2012; Bichel et al., 2013; and Matreyek et al., 2013).

Figure 1B:
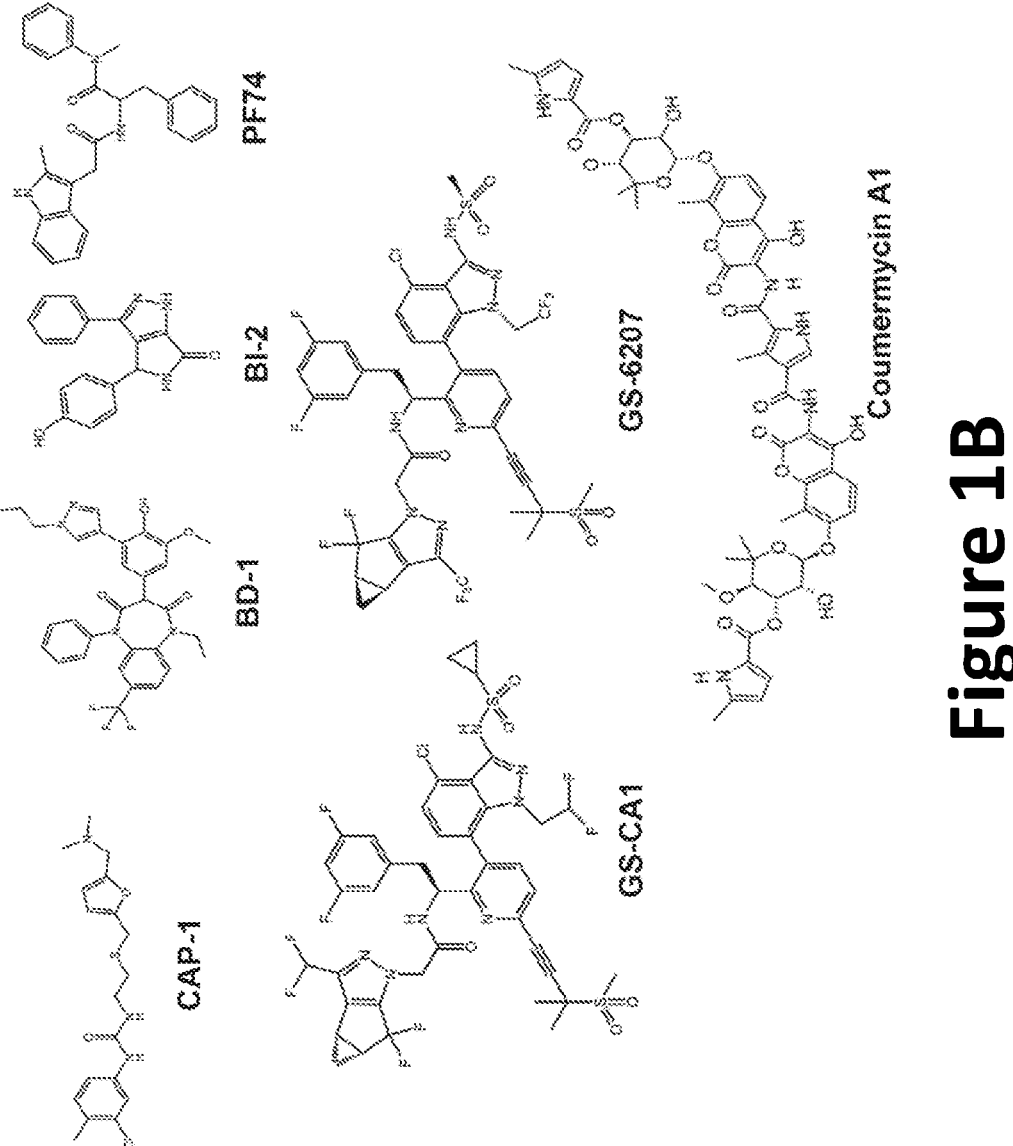

Given the role of CA in multiple steps of viral replication, it is an attractive antiviral target, offering novel strategies for therapeutic intervention (Prevelige, 2011; Bocanegra et al. 2012; and Li et al., 2013). Several drug-like compounds that bind at the CA-NTD or CA-CTD have been identified (Tang et al., 2003; Sticth et al., 2005; Ternois et al., 2005; Kelly et al., 2007; Blair et al., 2010; Curreli et al., 2011; and Bocanegra et al., 2012). Among these are benzodiazepine (BD) and benzimidazole (BM) compounds (Fader et al., 2011; Lemke et al., 2012; Tremblay et al., 2012), pyrrolopyrazolones (BI-1 and BI-2) (Lamorte et al., 2013), and CAP-1 (Kelly et al., 2007 and Curreli et al., 2011). One of the most well-studied CA inhibitors is PF-3450074 (PF74) (FIG. 1B). The crystal structures of PF74 bound to CA (Blair et al., 2010; Bhattacharya et al., 2014; and Price et al., 2014) have shown that PF74 occupies a pocket located between the CA-NTD and CA-CTD. This binding pocket is also shared by small molecule BI-2, as well as the host factors CPSF6 and NUP153 (Price et al., 2014). Therefore, both PF74 and BI-2 are expected to prevent the interaction between CA and CPSF6 or NUP153 (Price et al., 2012 and Price et al., 2014). PF74 appears to modulate inter-subunit interactions, perturb capsid assembly, and increase the rate of CA multimerization in vitro. PF74 interferes with both early and late events of the HIV replication cycle (Blair et al., 2010 and Thenin-Houssier and Valente, 2016). The accumulation of late reverse transcription products, 2LTRs, and integrated provirus suggests antiviral activity of PF74 at early steps in viral replication (Blair et al., 2010; Shi et al., 2011; and Fricke et al., 2014), whereas disruption of the formation of native-like particles indicates additional roles of PF74 at later stages of HIV replication (Blair et al., 2010; Thenin-Houssier and Valente, 2016). In addition to above-mentioned chemical inhibitors, peptide inhibitors (such as NYAD-1) have also been reported. NYAD-1 disrupts the formation of both immature- and mature-like virus particles in cell-based assembly assays (Zhang et al., 2013). Despite promising leads, none of these compounds or their derivatives have advanced to clinical trials.

Recently reported CA inhibitors GS-CA1 and GS6207 (an analog of GS-CA1, also called GS-CA2) (FIG. 1B) have greater potency than currently approved anti-HIV drugs (Blair et al., 2010; Tse et al., 2017; and Zheng et al., 2018). GS-CA1 inhibits HIV-1 replication in T cells and peripheral blood mononuclear cells (PBMCs) at very low concentrations ($EC_{50}$=240 pM and 140 pM, respectively). GS-6270 displays anti-HIV activity in MT-4 cells with an $EC_{50}$ of 100 pM, whereas in PBMCs, it displays a mean $EC_{50}$ of 50 pM (20-160 pM) against 23 HIV-1 clinical isolates from different subtypes (Zheng et al., 2018). In comparison, the most studied capsid inhibitor, PF74, displays a subtype-dependent range of EC50 between 80 nM and 640 nM in PBMCs. In MT-2 cells, the EC50 of PF74 is 570 nM (Blair et al., 2010). In addition, studies in rats and dogs indicate that a single subcutaneous injection maintains GS-CA1 and GS-6207 plasma concentrations above the plasma-binding-adjusted effective concentration required for 95% HIV-1 replication inhibition for >12 weeks, indicating their potential as a long-acting drug (Jarvis, 2017; Tse et al, 2017; Carnes et al., 2018; and Sager et al., 2019). Similar to PF74, GS-CA1 inhibits both early and late stages of virus replication.

Still, there remains a need to discover new antivirals acting through novel mechanisms and/or directed to new targets.

SUMMARY

This disclosure is drawn to a cyclic or linear peptide comprising the amino acid sequence of F-$X^1$F-$X^2$-P-V-$X^3$-F (SEQ ID NO: 2), wherein $X^1$, $X^2$, and $X^3$ are each independently glycine (G), lysine (K), or a polar uncharged amino acid. In certain aspects, $X^2$ is glycine and $X^1$ and $X^3$ are each a polar uncharged amino acid. In certain aspects, $X^1$ is threonine (T) and/or $X^3$ is asparagine (R). Thus, in certain aspects, $X^1$ is threonine (T) and/or $X^3$ is asparagine (R) and $X^2$ is glycine.

This disclosure is also drawn to the cyclic or linear peptide above, wherein the peptide comprises the amino acid sequence of $X^4$-$X^5$-$X^6$-F-$X^1$-F-$X^2$-P-V-$X^3$-F-$X^7$-$X^8$ (SEQ ID NO: 3), and wherein $X^4$, $X^5$, $X^6$, $X^7$, and $X^8$ are each independently selected from the group consisting of glycine (G), proline (P), lysine (K), a polar uncharged amino acid, and a hydrophobic amino acid. In certain aspects; $X^4$ is a polar uncharged amino acid such a serine (S); $X^6$ is a hydrophobic amino acid such as valine (V); $X^7$ is proline (P); and/or $X^5$ and/or $X^8$ are glycine (G).

In certain aspects of the above peptides, at least one of $X^1$, $X^2$, $X^3$, $X^4$, $X^5$, $X^6$, $X^7$, or $X^8$ is lysine (K).

This disclosure is also drawn to a cyclic or linear peptide, wherein the peptide comprises or consists of the amino acid sequence S-G-V-F-T-F-G-P-V-N-F-P-G (SEQ ID NO: 4) or S-G-V-F-Y-F-W-P-V-N-F-P-G (SEQ ID NO: 5).

In certain aspects of any of the above peptides, the peptide further comprises one or more additional amino acids, wherein at least one of the additional amino acids is lysine (K).

This disclosure is also drawn to a cyclic or linear peptide comprising or consisting of an amino acid sequence of S-G-V-F-T-F-G-P-V-N-F-P-G (SEQ ID NO: 4) or S-G-V-F-Y-F-W-P-V-N-F-P-G (SEQ ID NO: 5), except wherein the sequence has one or two changes selected from an amino acid substitution, a single amino acid addition; a single amino acid deletion, or a combination of two thereof. In certain aspects, the sequence has one or two amino acid substitutions but not an amino acid addition or amino acid deletion. In certain aspects, the sequence has only one amino acid substitution. And, in certain aspects, the amino acid substitution is a conservative amino acid substitution.

In certain aspects of any of the above peptides, the peptide further comprises a dye, a chelator, a radionuclide, or any combination of a dye, a chelator, and a radionuclide.

In certain aspects of any of the above peptides, the peptide binds to an HIV-1 capsid protein. In certain aspects, the peptide binds to a binding pocket of the HIV-1 capsid protein located between the C-terminus domain (CTD) and the N-terminus domain (NTD) of the capsid protein. In certain aspects, the HIV-1 capsid protein has an amino acid sequence comprising:

(SEQ ID NO: 1)

PIVQNLQGQMVHQAISPRTLNAWVKVIEEKAFSPEVIPMFTALSEGATPQ

DLNTMLNTVGGHQAAMQMLKDTINEEAAEWDRLHPVHAGPIAPGQMREPR

GSDIAGTTSTLQEQIAWMTSNPPIPVGDIYKRWIILGLNKIVRMYSPVSI

LDIKQGPKEPFRDYVDRFFKTLRAEQATQDVKNWMTDTLLVQNANPDCKT

ILRALGPGATLEEMTACQGVGGPSHKARVL and the peptide interacts with a residue of the capsid protein comprising L56 of SEQ ID NO: 1, N57 of SEQ ID NO: 1, M66 of SEQ ID NO: 1, or a combination of any thereof. In certain aspects, the peptide has a binding affinity for the HIV-1 capsid protein that is at least about 2-fold higher, at least about 3-fold higher, at least about 4-fold higher, at least about 5-fold higher, at least about 6-fold higher, at least about 7-fold higher, at least about 8-fold higher, at least about 9-fold higher, or at least about 10-fold higher than capsid inhibitor PF74. In certain aspects, the peptide inhibits an HIV-1 capsid from assembling and/or disassembling. In certain aspects, the peptide has an $IC_{50}$ of about 2 μM to about 4 μM. In certain aspects, the peptide has an $IC_{50}$ of about 3.2 μM.

In certain aspects of any of the above peptides, the peptide has a length of 50 amino acids or fewer, 40 amino acids or fewer, 30 amino acids or fewer, 25 amino acids or fewer, 20 amino acids or fewer, 19 amino acids or fewer, 18 amino acids or fewer, 17 amino acids or fewer, 16 amino acids or fewer, 15 amino acids or fewer, 14 amino acids or fewer, 13 amino acids or fewer, 12 amino acids or fewer, 11 amino acids or fewer, 10 amino acids or fewer, 9 amino acids or fewer, or has a length of 8 amino acids.

In certain aspects, the peptide is a linear peptide.

In certain aspects, the peptide is a cyclic peptide. Further provided is a method of producing the cyclic peptide of this disclosure, the method comprising producing a linear peptide of the sequence desired for the cyclic peptide and cyclizing the linear peptide to produce the cyclic peptide. In certain aspects, the linear peptide is chemically synthesized. In certain aspects, the linear peptide is translated in a host cell. Thus, also provides is an isolated polynucleotide comprising a nucleic acid which encodes any peptide of this disclosure. In certain aspects, the isolated polynucleotide further comprises a heterologous nucleic acid. In certain aspects, the heterologous nucleic acid comprises a promoter operably associated with the nucleic acid encoding the peptide. Certain aspects provide for a vector comprising any of the above polynucleotides. In certain aspects, the vector is a plasmid. Certain aspects also provide for a host cell comprising such vector, such as a bacterium, an insect cell, a mammalian cell or a plant host cell.

Also provide for herein is a pharmaceutical composition comprising any peptide of this disclosure and a method of treating an HIV infection in a subject in need thereof, the method comprising administering a therapeutically effective amount of the composition to the subject.

BRIEF DESCRIPTION OF THE DRAWINGS/FIGURES

FIGS. 1A,B. FIGS. 1A and 1B show the structure of HIV-1 CA protein and representative CA inhibitors. (A) This figure was generated from the X-ray crystal structure of native HIV-1 capsid protein bound to PF74 (PDB entry 4XZF) (Gres et al. 2015). NTD: N-terminal domain, CA-CTD: C-terminal domain. (B) Chemical structures of selective CA inhibitors. The structures of CA inhibitors shown here have either been solved in complex with CA, or we have used them in docking protocols.

FIGS. 2A-D. FIG. 2 shows a molecular model of CA/GS-CA1 complex. (A) Docked pose of GS-CA1 in CA-hexamer (only dimer shown). (B) Close up of predicted GS-CA1 binding site in CA-hexamer. The side chains of CA and GS-CA1 are rendered as ball-and-stick. The backbone of CA is rendered as ribbons. Residues with orange carbons depict GS-CA1 resistance mutation positions (Perrier et al., 2017). (C) A detailed view of these residues and their proximity to GS-CA1. (D) Other residues of CA that interact with GS-CA1. GS-CA1 carbons in this and in subsequent figures are shown as green. The nitrogen, oxygen, sulphur and fluorine atoms are colored blue, red, yellow and aquamarine, respectively.

FIGS. 3A-E. (A) Superposition of GS-CA1 and GS-6207. The switched position of cyclopenta-pyrazole ring is shown by dotted circle. (B) Difference in the side chain conformations of K70 and R173 between CA/GS-CA1 and CA/GS-6207 complexes. Solid arrow shows the displacement of atom of K73 in two complexes, whereas the dotted line shows the H-bond formed by GS-6207 with K70. This interaction is missing in CA/GS-CA1 complex. (C) Superposition of CA/PF74 crystal structure (PDB entry 4XZF) on the molecular model of CA/GS-CA1. The resistance mutations associated with PF74 close to the binding pocket are shown in cyan carbons. GS-CA1 resistance associated residues are depicted as in FIG. 2. (D) Approximately 45° rotated view of Panel A. Dotted circles show superposition of three structural components of GS-CA1 and PF74. (E) Superposition of GS-CA1, PF74 and BI-2.

FIGS. 4A,B. (A) Superposition of CA/CP SF6 crystal structure on the molecular model of CA/GS-CA1. For clarity, residues P313-P316 and backbone atoms of CPSF6 have been omitted. This figure shows the superposition of the difluorobenzyl ring of GS-CA1 on F321 of CPSF6. (B) Superposition of CA/NUP153 crystal structure complex on the molecular model of CA/GS-CA1. For clarity, only residues F1415-G1418 are shown. This figure shows the superposition of the difluorobenzyl ring of GS-CA1 on F1417 of NUP153. In addition, F1415 of NUP153 and the methylsulfonyl group of GS-CA1 have a common interaction with P38 of CA-hexamer. The atoms of P38 are not shown for clarity.

Figure 5:
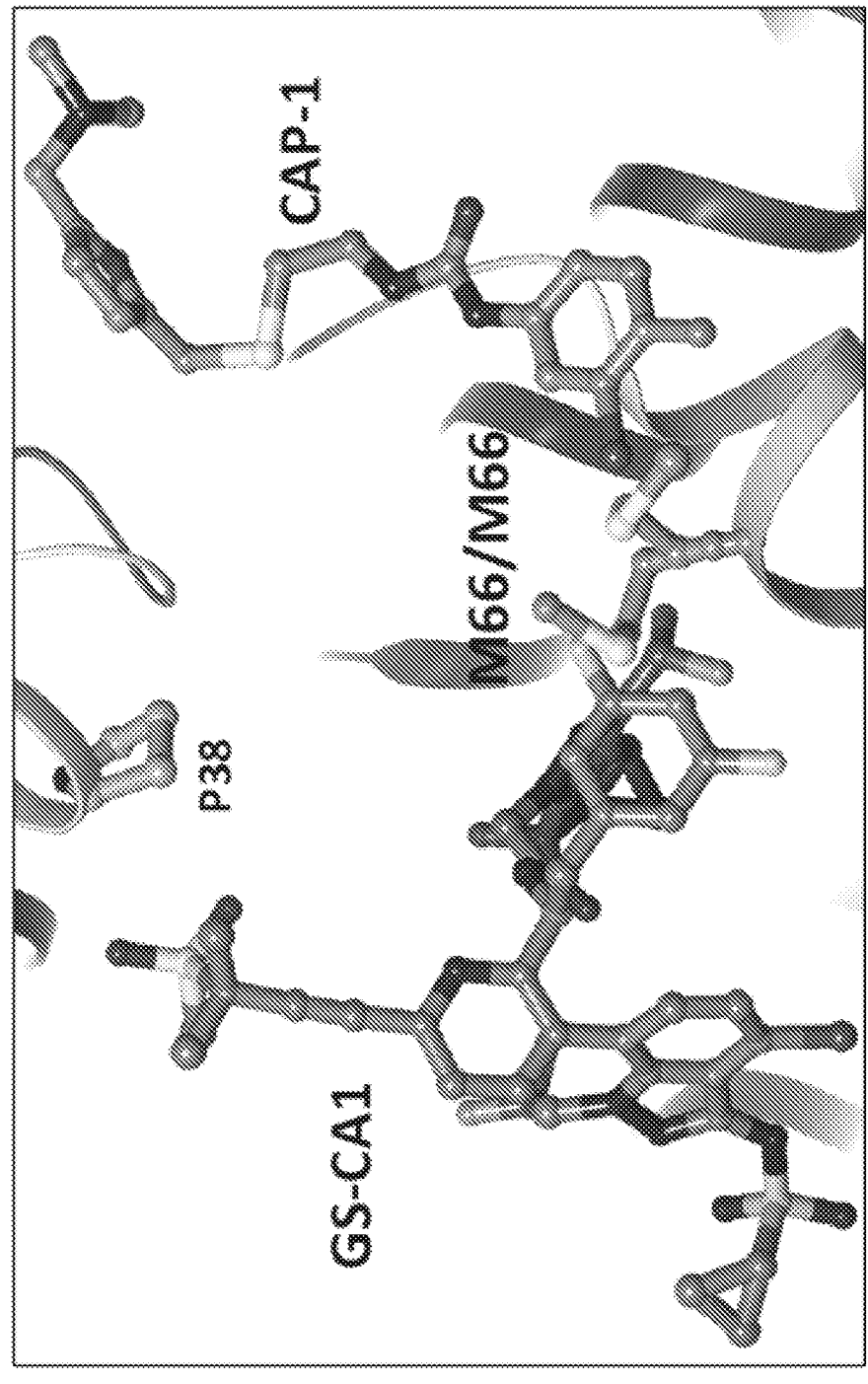

FIG. 5. Superposition of CA/CAP-1 crystal structure complex on the molecular model of CA/GS-CA1. For clarity, only M66 in the two structures is shown (orange—CA/GS-CA1; teal—CA/CAP-1).

Figure 6:
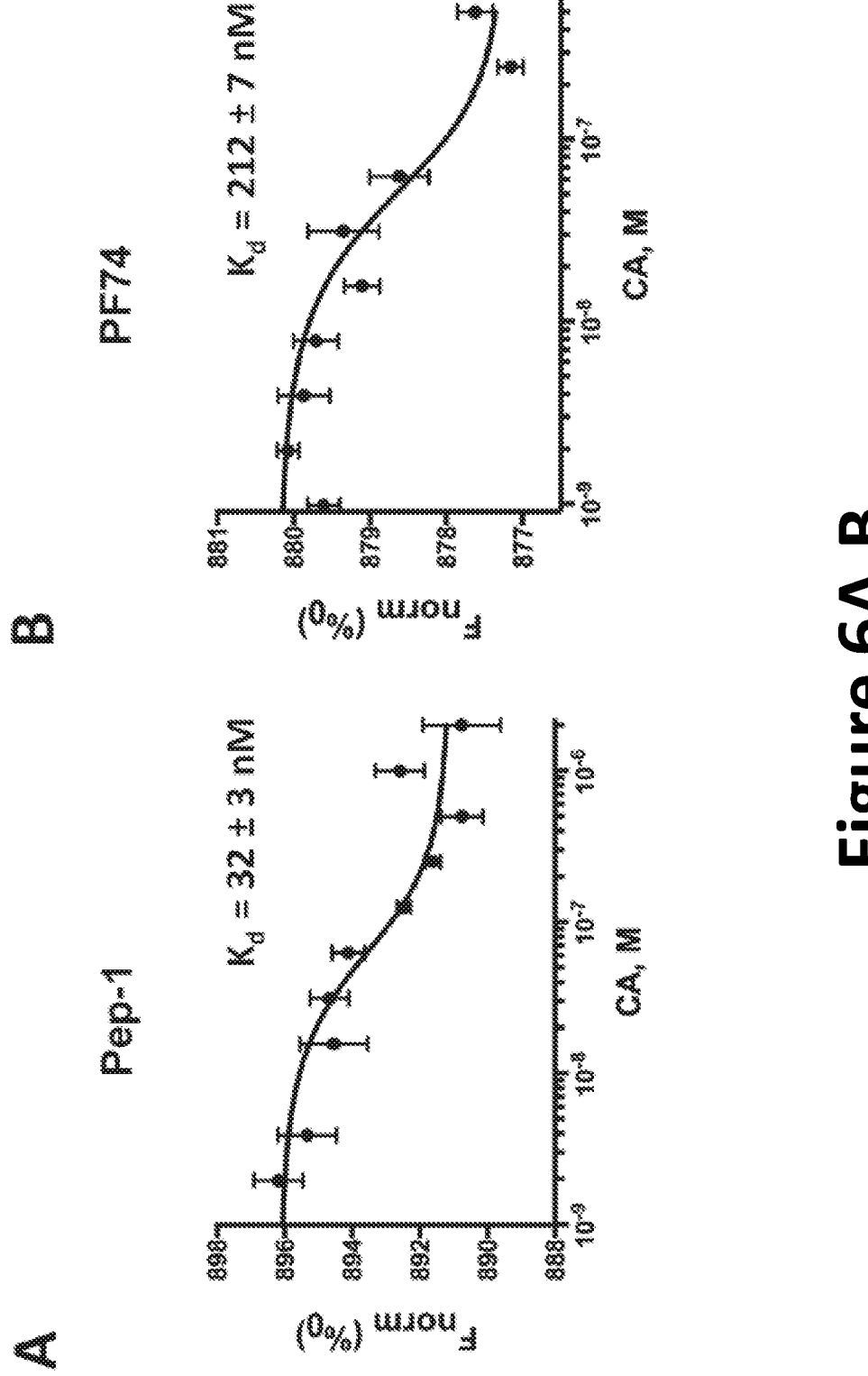

FIGS. 6A,B. FIG. 6 shows that Pep-2-cyclic binds HIV-1 capsid better than well studied inhibitor PF74. Pep-2-cyclic (A) and PF74 (B) binding affinities of CA as determined by MicroScale Thermophoresis. This figure shows the change in fluorescence due to thermophoresis at the increasing concentrations of Pep-2-cyclic and PF74 (1 nM to 2000 nM) in the presence of 200 nM CA-hexamers.

Figure 7:
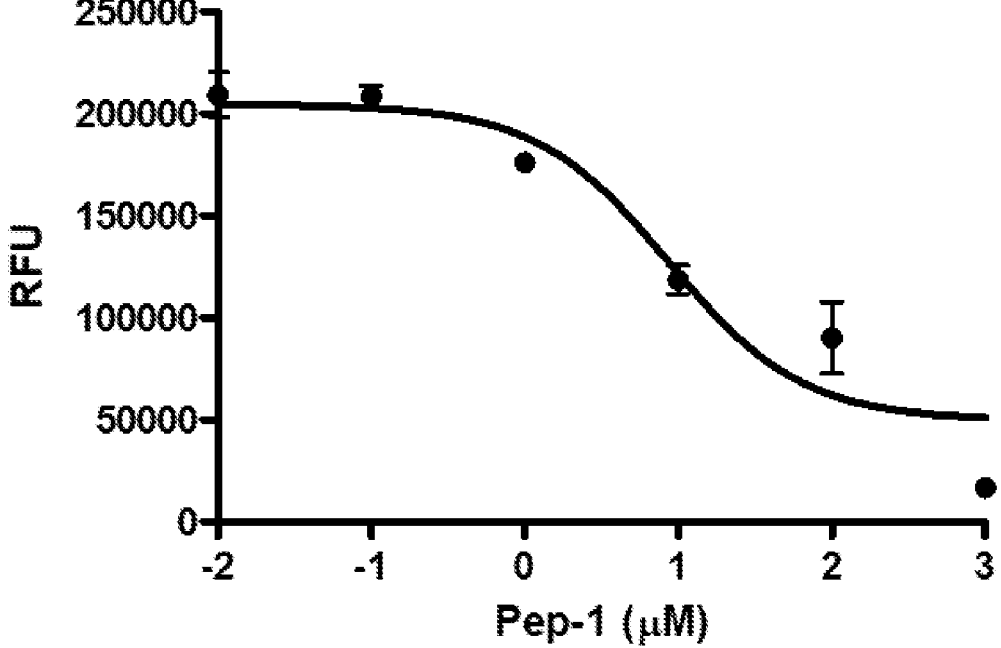

FIG. 7. FIG. 7 shows inhibitory activity of Pep-2-cyclic in cell culture.

Figure 8:
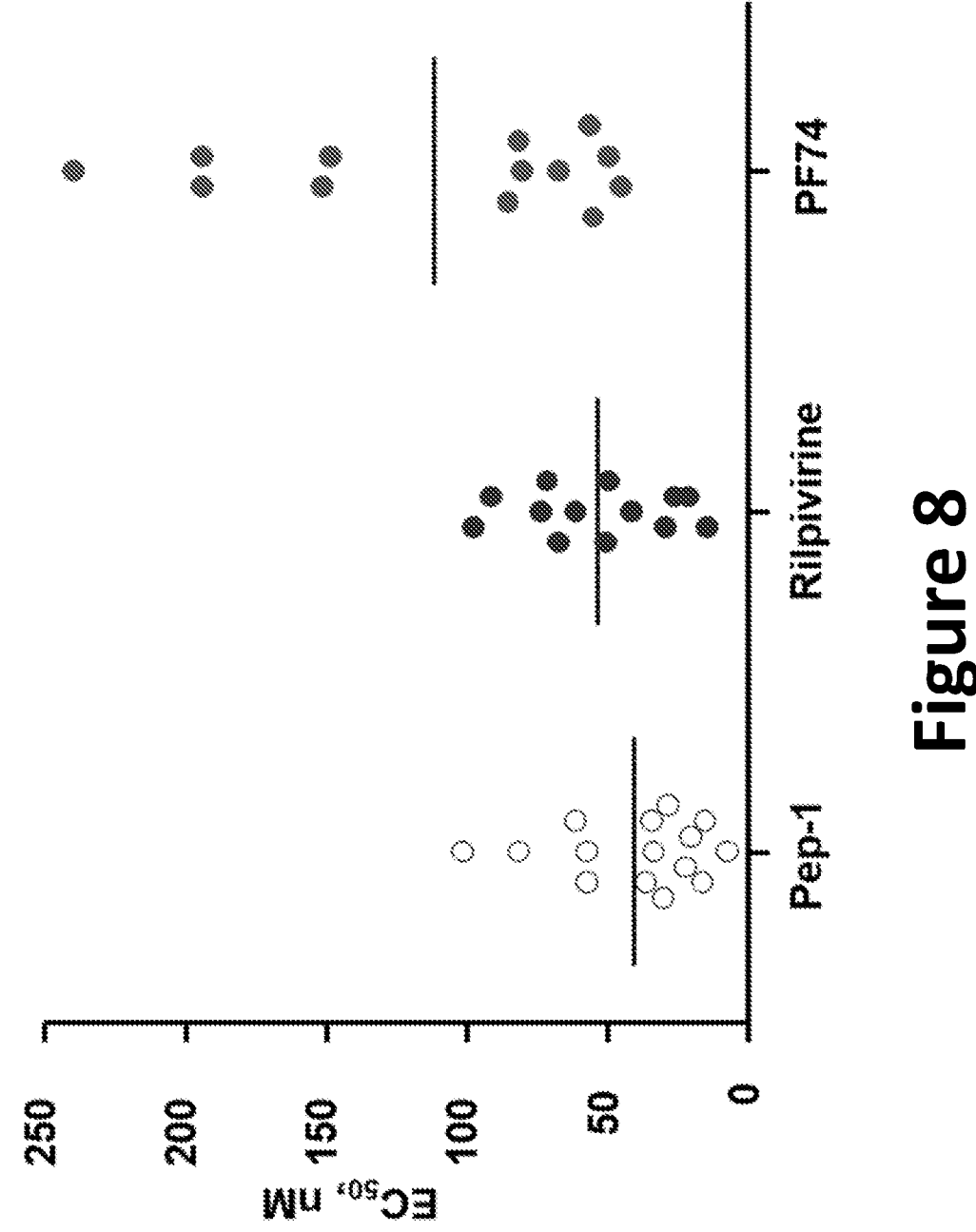

FIG. 8. FIG. 8 shows inhibitory activity of Pep-2-cyclic in humanized mouse model compared to approved drug Rilpivirine (NNRTI) and capsid inhibitor PF74. Pep-2-cyclic inhibits HIV-1 with an $EC_{50}$ comparable to rilpivirine but lot better than most studied capsid inhibitor PF74 (line represents median $EC_{50}$) (results from 15 mice)—two each in Rilpivirine and PF74 arms were euthanized and one in Pep-2-cyclic arm died.

Figure 9:
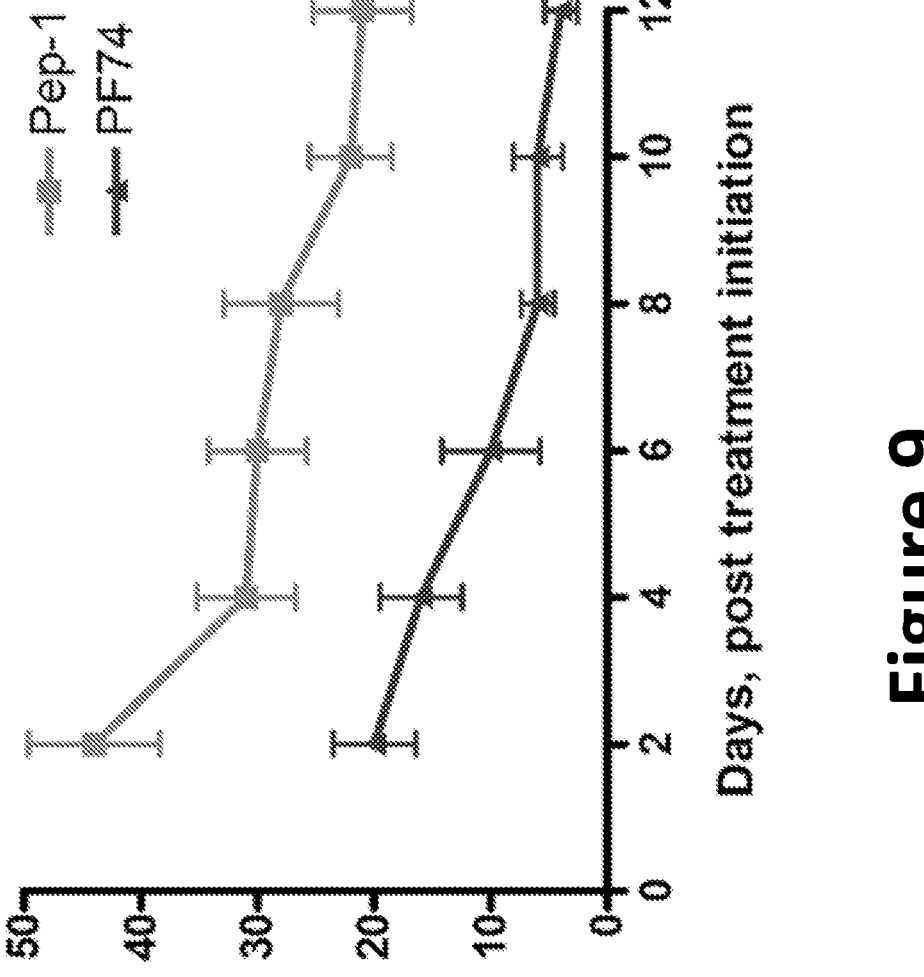

FIG. 9. FIG. 9 shows a plasma Pep-2-cyclic and PF74 concentrations over time in efficacy study. Symbols are mean±SD fold over the mouse serum protein-binding-adjusted EC95 (paEC95) values for each compound (results from 3 mice).

FIG. 10. FIG. 10 is a list of representative peptide sequences of the disclosure.

DETAILED DESCRIPTION

Definitions

It is to be noted that the term "a" or "an" entity refers to one or more of that entity; for example, "a cyclic peptide," is understood to represent one or more cyclic peptides. As such, the terms "a" (or "an"), "one or more," and "at least one" can be used interchangeably herein.

Furthermore, "and/or" where used herein is to be taken as specific disclosure of each of the specified features or components with or without the other. Thus, the term and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

It is understood that wherever aspects are described herein with the language "comprising" or "comprises" otherwise analogous aspects described in terms of "consisting of," "consists of," "consisting essentially of," and/or "consists essentially of" and the like are also provided.

Unless defined otherwise, technical and scientific terms used herein have the same meaning as commonly understood by one of ordinary skill in the art to which this disclosure is related.

Numeric ranges are inclusive of the numbers defining the range. Even when not explicitly identified by "and any range in between," or the like, where a list of values is recited, e.g., 1, 2, 3, or 4, unless otherwise stated, the disclosure specifically includes any range in between the values, e.g., 1 to 3, 1 to 4, 2 to 4, etc.

The headings provided herein are solely for ease of reference and are not limitations of the various aspects or aspects of the disclosure, which can be had by reference to the specification as a whole.

As used herein, the term "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids are included within the definition of "polypeptide," and the term "polypeptide" can be used instead of, or interchangeably with any of these terms. The term "polypeptide" is also intended to refer to the products of post-expression modifications of the polypeptide, including without limitation glycosylation, acetylation, phosphorylation, amidation, derivatization by known protecting/blocking groups, proteolytic cleavage, or modification by non-standard amino acids. A polypeptide can be derived from a natural biological source or produced by recombinant technology, but is not necessarily translated from a designated nucleic acid sequence. It can be generated in any manner, including by chemical synthesis.

A used herein, a "cyclic peptide" refers to a peptide which instead of consisting of a linear amino acid sequence, is cyclized. For example, in certain aspects, a cyclic peptide can be formed via a lactame bond between the carboxylic C-terminus and the amine N-terminus.

A used herein, a "polar uncharged amino acid" refers to an amino acid having a side chain bearing a polar chemical function different than a charged one. Thus, polar uncharged amino acids include: serine (S), threonine (T), cysteine (C), asparagine (N), glutamine (Q), and tyrosine (Y).

As used herein, a "hydrophobic amino acid" refers to an amino acid having a hydrophobic side chain. Thus hydrophobic amino acids include: glycine (G), alanine (A), valine (V), leucine (L), isoleucine (I), proline (P), phenylalanine (F), methionine (M), and tryptophan (W).

A "protein" as used herein can refer to a single polypeptide, i.e., a single amino acid chain as defined above, but can also refer to two or more polypeptides that are associated, e.g., by disulfide bonds, hydrogen bonds, or hydrophobic interactions, to produce a multimeric protein.

By an "isolated" polypeptide or a fragment, variant, or derivative thereof is intended a polypeptide that is not in its natural milieu. No particular level of purification is required. For example, an isolated polypeptide can be removed from its native or natural environment. Recombinantly produced polypeptides and proteins expressed in host cells are considered isolated as disclosed herein, as are recombinant polypeptides that have been separated, fractionated, or partially or substantially purified by any suitable technique.

The term "polynucleotide" is intended to encompass a singular nucleic acid as well as plural nucleic acids, and refers to an isolated nucleic acid molecule or construct, e.g., messenger RNA (mRNA) or plasmid DNA (pDNA). A polynucleotide can comprise a conventional phosphodiester bond or a non-conventional bond (e.g., an amide bond, such as found in peptide nucleic acids (PNA)). The term "nucleic acid" refers to any one or more nucleic acid segments, e.g., DNA or RNA fragments, present in a polynucleotide. By "isolated" nucleic acid or polynucleotide is intended a nucleic acid molecule, DNA or RNA, which has been removed from its native environment. For example, a recombinant polynucleotide encoding a polypeptide subunit contained in a vector is considered isolated as disclosed herein. Further examples of an isolated polynucleotide include recombinant polynucleotides maintained in heterologous host cells or purified (partially or substantially) polynucleotides in solution. Isolated RNA molecules include in vivo or in vitro RNA transcripts of polynucleotides. Isolated polynucleotides or nucleic acids further include such molecules produced synthetically. In addition, polynucleotide or a nucleic acid can be or can include a regulatory element such as a promoter, ribosome binding site, or a transcription terminator.

In certain embodiments, the polynucleotide or nucleic acid is DNA. In other embodiments, a polynucleotide can be RNA.

The term "sequence identity," to a reference sequence, or a sequence that is a % "identical to," a reference sequence, and like, as used herein refers to a relationship between two or more polynucleotide sequences or between two or more polypeptide sequences. When a position in one sequence is occupied by the same nucleic acid base or amino acid in the corresponding position of the comparator sequence, the sequences are said to be "identical" at that position. The percentage "sequence identity" is calculated by determining the number of positions at which the identical nucleic acid base or amino acid occurs in both sequences to yield the number of "identical" positions. The number of "identical" positions is then divided by the total number of positions in the comparison window and multiplied by 100 to yield the percentage of "sequence identity." Percentage of "sequence identity" is determined by comparing two optimally aligned sequences over a comparison window and a reference polynucleotide or polypeptide. In order to optimally align sequences for comparison, the portion of a polynucleotide or polypeptide sequence in the comparison window can comprise additions or deletions termed gaps while the reference sequence is kept constant. An optimal alignment is that alignment which, even with gaps, produces the greatest possible number of "identical" positions between the reference and comparator sequences. Percentage "sequence identity" between two sequences can be determined using the version of the program "BLAST 2 Sequences" which is available from the National Center for Biotechnology Information as of Sep. 1, 2004, which program incorporates the programs BLASTN (for nucleotide sequence comparison) and BLASTP (for polypeptide sequence comparison), which programs are based on the algorithm of Karlin and Altschul (Proc. Natl. Acad. Sci. USA 90(12):5873-5877, 1993). When utilizing "BLAST 2 Sequences," parameters that were default parameters as of Sep. 1, 2004, can be used for word size (3), open gap penalty (11), extension gap penalty (1), gap drop-off (50), expect value (10) and any other required parameter including but not limited to matrix option.

A "vector" is nucleic acid molecule as introduced into a host cell, thereby producing a transformed host cell. A vector can include nucleic acid sequences that permit it to replicate in a host cell, such as an origin of replication. A vector can also include one or more selectable marker gene and other genetic elements known in the art.

A "transformed" cell, or a "host" cell, is a cell into which a nucleic acid molecule has been introduced by molecular biology techniques. As used herein, the term transformation encompasses those techniques by which a nucleic acid molecule can be introduced into such a cell, including transfection with viral vectors, transformation with plasmid vectors, and introduction of naked DNA by electroporation, lipofection, and particle gun acceleration. A transformed cell or a host cell can be a bacterial cell or a eukaryotic cell.

The term "expression" as used herein refers to a process by which a gene produces a biochemical, for example, a polypeptide. The process includes any manifestation of the functional presence of the gene within the cell including, without limitation, gene knockdown as well as both transient expression and stable expression. It includes without limitation transcription of the gene into messenger RNA (mRNA), and the translation of such mRNA into polypeptide(s). If the final desired product is a biochemical, expression includes the creation of that biochemical and any precursors. Expression of a gene produces a "gene product."

As used herein, a gene product can be either a nucleic acid, e.g., a messenger RNA produced by transcription of a gene, or a polypeptide that is translated from a transcript. Gene products described herein further include nucleic acids with post transcriptional modifications, e.g., polyadenylation, or polypeptides with post translational modifications, e.g., methylation, glycosylation, the addition of lipids, association with other protein subunits, proteolytic cleavage, and the like.

As used herein the terms "treat," "treatment," or "treatment of" (e.g., in the phrase "treating a subject") refers to reducing the potential for disease pathology, reducing the occurrence of disease symptoms, e.g., to an extent that the subject has a longer survival rate or reduced discomfort. For example, treating can refer to the ability of a therapy when administered to a subject, to reduce disease symptoms, signs, or causes. Treating also refers to mitigating or decreasing at least one clinical symptom and/or inhibition or delay in the progression of the condition and/or prevention or delay of the onset of a disease or illness.

By "subject" or "individual" or "animal" or "patient" or "mammal," is meant any subject, particularly a mammalian subject, for whom diagnosis, prognosis, or therapy is desired. Mammalian subjects include humans, domestic animals, farm animals, sports animals, and zoo animals, including, e.g., humans, non-human primates, dogs, cats, guinea pigs, rabbits, rats, mice, horses, cattle, bears, and so on.

The term "pharmaceutical composition" refers to a preparation that is in such form as to permit the biological activity of the active ingredient to be effective, and that contains no additional components that are unacceptably toxic to a subject to which the composition would be administered. Such composition can be sterile.

An "effective amount" of an antibody as disclosed herein is an amount sufficient to carry out a specifically stated purpose (e.g., "therapeutically effective amount"). An "effective amount" can be determined empirically and in a routine manner, in relation to the stated purpose.

As referred to herein, "a/the cyclic or linear peptide of this disclosure" and the like refers to any and all aspects or embodiments of a cyclic or linear peptide described herein, unless otherwise specified.

As used herein, HIV-1 capsid "assembling" means the formation of capsid core from multiple subunits and "disassembling" means dissolution of the capsid core to release HIV genome into the cytoplasm.

Overview

The crystal structure of GS-CA1-bound CA hexamer has been reported but not made publicly available. Reportedly, GS-CA1 binds CA at the same general site as PF74, CPSF6, and NUP153 (Tse et al., 2017). The crystal structure of CA in complex with GS-6207 is yet to be reported. Although no well-understood, GS-CA1 and GS-6207 possibly interact more extensively with CA than PF74, providing greater binding affinity and thereby, greater efficacy than PF74. Here, using computational approaches and reported inhibitor-bound CA structures, we present the details of interactions between GS-CA compounds and CA. We find the GS-CA compounds contain similar features that are also present in PF74, BI-2, NUP153, and CPSF6. Using the same structural features in our computational modeling, we designed a cyclic peptide (Pep-2-cyclic), that docked at the GS-CA biding site with comparable docking score. We validated the binding of Pep-2-cyclic to CA by determining CA binding affinity of Pep-2-cyclic using MicroScale Thermophoresis (MST) experiments, which revealed that CA binds Pep-2-cyclic with ~7-fold better affinity than PF74, a well-known CA inhibitor.

Interactions of GS-CA1 and GS-6207 with CA in modeled CA/GS-CA complexes

To gain insights into the interactions between the CA hexamer and GS-CA1, Induced-Fit Docking (IFD) interfaced with Maestro of Schrodinger Suite (Schrodinger LLC, NY) was used (Examples). A docked pose of GS-CA1 (with best Glide score) in the crystal structure of the native form of CA-hexamer (PDB entry 4XFZ) (Gres et al., 2015) is shown in FIG. 2. This figure shows that GS-CA1 binds in the close proximity to residues L56, M66, Q67, N74 and A105 (FIG. 2B and FIG. 2C). In vitro selection studies have identified GS-CA1 resistance mutations L56I, M66I, Q67H, N74D and A105E (Perrier et al., 2017), suggesting that these mutations may affect GS-CA1 binding to the CA hexamer. Notably, IFD docking was conducted without any bias towards L56, M66, Q67, L74 or A105. In addition, in our model of the CA/GS-CA1 complex, CA-NTD residues I37, P38, S41, N53, T54, N57, Q63, L69, K70, I73, T106, T107, Y130, Y169, L172, R173 and Q179 also directly interact with GS-CA1 (FIG. 2D). Many of these residues are critical to binding of small molecules or peptides derived from host factors CPSF6 and NUP153 (Price et al., 2014).

In a limited size cohort (n=15), the antiviral activity of GS-CA1 was reported to be comparable among clinical isolates from different subtypes (Tse et al., 2017), suggesting a strong conservation of amino acid residues in the GS-CA1 binding pocket. To assess whether the GS-CA1 binding pocket is conserved among subtypes, a consensus sequence was generated of CA from HIV-1 subtype C (HIV-1C), which accounts for more than 50% of all HIV-1 infections, using the Los Alamos HIV sequence database (world wide web at https://www.hiv.lanl.gov). The results showed that the GS-CA1 binding site in HIV-1C was highly conserved. Only one substitution in HIV-1C (F169) compared to HIV-1B (Y169) was noted. The nearest (Cδ) atom of Y169 (or F169 in HIV-1C) is within interacting distance of GS-CA1 (<3.8 Å), suggesting a weak interaction with GS-CA1.

GS-6207 differs from GS-CA1 by three modifications: (i) a cyclopropane moiety on sulfonamide group was replaced by a methyl group, (ii) difluoroethyl groups on indazole ring was replaced by a trifluoroethyl group, and (iii) difluoromethyl group on cyclopenta-pyrazole ring was replaced by a trifluoromethyl moiety. At present, the specific rationale for these replacements is not known. GS-6207 was docked in the crystal structure of native form of CA (Gres et al., 2015). The results showed that GS-6207 binds in the same binding pocket as GS-CA1 and with a slightly better Glide score (−14.362 for GS-6207 versus −11.271 for GS-CA1), suggesting a better binding affinity. It was also noted that the orientation of cyclopenta-pyrazole ring in docked GS-6207 was switched by ~180° compared to that in GS-CA1, leading to the exposure of trifluoromethyl moiety to the solvent (FIG. 3A). Another remarkable difference between docked complexes of CA/GS-CA1 and CA/GS-6207 is the conformation of K70 and R173 side chains. In CA/GS-6207 complex, K70 side chain moves around 5 Å from the position in CA/GS-CA1 complex (FIG. 3B, solid arrow) towards the binding pocket and forms a hydrogen bond with C=O of amide group in GS-6207 (FIG. 3B, dotted line). An additional H-bond may be one of the reasons that GS-6207 has better Glide score than GS-CA1. While the side chain conformation of R173 is also altered (FIG. 3B), it does not appear to be significant.

Comparison with PF74/CA and BI-2/CA Crystal Structures

Five mutations (Q67H, K70R, T107N, L111I and H87P) confer resistance to PF74 (Blair et al., 2010; Shi et al., 2011; Shi et al. 2015; and Zhou et al., 2015). Residues Q67, K70, T107 and L111 reside on helices 4 and 5, whereas H87 is part of the CypA binding loop (residues 85-93) (Gamble et al., 1996; and Ambrose and Aiken, 2014). The only common resistance mutation between GS-CA1 and PF74 is Q67H (Perrier et al., 2017), although other GS-CA1 resistance residues (L56, M66, L74, and A105) are also within interacting distance of PF74. A superposition of the CA/PF74 crystal structure (Gres et al., 2015) and the CA/GS-CA1 model is shown in FIG. 3C. It is clear from the figure that all three rings of PF74 (two phenyl rings and one indole ring) superpose extremely well on three different rings GS-CA1 (dotted circles 1, 2 and 3 in FIG. 3D). The PF74 indole ring superposes on the cyclopenta-pyrazole ring of GS-CA1 (circle 1). One of the two phenyl rings of PF74 superposes on the difluorobenzene ring of GS-CA1 (circle 2), whereas the other PF74 phenyl ring is at a topologically similar position to the indazole ring of GS-CA1 (circle 3). Additionally, the polar moieties of PF74 match topologically with the polar moieties of GS-CA1. Thus, the acetamide moiety of GS-CA1 superposes well on the corresponding moiety of PF74. These data suggest that certain structural features and interactions are common between GS-CA1 and PF74.

During IFD of GS-CA1 into the CA-hexamer, the conformations of most of the side chains in the GS-CA1/PF74 binding pocket did not change significantly as compared to the CA/PF74 crystal structure, with the exception of the side chain of K70 (FIG. 3C). The position of the K70 atom was shifted by ~4.7 Å from its position in the CA/PF74 complex (FIG. 3C), suggesting an absence of interactions between K70 and GS-CA1, in contrast to K70 interactions with PF74. The absence of this interaction is a possible reason that mutation at K70 did not emerge during GS-CA1 in vitro resistance selection studies (Perrier et al., 2017). As mentioned above, the interaction of K70 is restored in the CA/GS-6207 complex. At present, the resistance mutation profile of GS-6207 is not known.

BI-2 is one of the two 4,5-dihydro-1H-pyrrolo[3,4-c] pyrazol-6-one series compounds shown to bind the CA hexamer. BI-2 was shown to stabilize CA hexamers and inhibit HIV-1 at early stages of infection (Lamorte et al., 2013). Selection of viruses resistant to BI-2 identified mutations at residues A105 and T107 of CA-NTD (Lamorte et al., 2013). The high-resolution structure of CA in complex with BI-2 showed that it binds at the PF74 binding site. The superposition of the three compounds (GS-CA1, PF74, and BI-2) obtained from the superposition of Ca-atoms of CA-NTD showed that the three compounds have a common binding mode with CA-hexamer (FIG. 3E). Docking results of GS-CA1 showed that CA residue A105 is within interacting distance of GS-CA1, and the common resistance mutation A105T between GS-CA1 and BI-2 further confirms that the two compounds share part of the binding site.

Comparison with CPSF6/CA and NUP153/CA Crystal Structures

The crystal structures of CA in complex with short peptides derived from CPSF6 and NUP153 showed that both peptides share the binding pocket occupied by PF74 and BI-2 (Price et al., 2014), although the bound peptides had additional interactions. To determine whether common structural features among GS-CA1, CPSF6, and NUP153 exist upon binding to CA, the crystal structures of CA/CPSF6 and CA/NUP153 were superimposed on the modeled CA/GS-CA1 complex. The superposition is shown in FIG. 4, demonstrating that the conformation of GS-CA1 docked into the CA-hexamer follows the folding of the CPSF6 peptide (FIG. 4A). The side chain of F321 of CPSF6 perfectly superposed on the difluorobenzyl moiety of GS-CA1.

Similar to CPSF6, the NUP153 backbone follows the conformation of GS-CA1, and F1417 of NUP153 perfectly superposes on the difluorobenzyl moiety of GS-CA1 (FIG. 4B). In addition, there exists a hydrophobic interaction between the methylsulfonyl moiety of GS-CA1 and P38 of CA (atoms of P38 are not shown). A similar interaction is noted between F1415 of NUP153 and P38 (FIG. 4B).

Comparison with CA/CAP-1, CA/BD and CA/BM Complexes

CAP-1 1-(3-chloro-4-methylphenyl)-3-(2-(((5-((dimethylamino)methyl)furan-2-yl)methyl)thio)ethyl)urea is an assembly inhibitor for which the resistance mutation profile has not been reported (Kelly et al., 2007). The structure of CAP-1 bound CA-NTD have been solved by NMR and X-ray crystallography (Kelly et al., 2007). A comparison of the crystal and NMR structures demonstrated that CA undergoes significant conformational change upon CAP-1 binding. The superposition of the crystal structure of the CA/CAP-1 complex on the model structure of the CA/GS-CA1 complex showed that the two inhibitors did not bind at a common site (FIG. 5). However, two residues (M66 and L69) interacted with both GS-CA1 and CAP-1. The positions of M66 in the CA/GS-CA1 and CA/CAP-1 complexes are shown in FIG. 5. The compounds of the benzodiazepine (BD1-BD4) and benzimidazole (BM1-BM5) series bind to CA at a site that is close to the CAP-1 binding site (Lemke et al., 2012). While compounds from both series have been shown to bind at the same pocket, they have distinct resistance mutation profiles. Mutations V36T and G61E were selected with BD inhibitors, whereas K30R and S33G were selected with BM inhibitors. Both V36 and G61 are part of BM3 binding pocket (PDB entry 4E91) (Sticht et al., 2005). K30 is not within interacting distance of BM4, and the backbone carbonyl group of S33 forms only forms a Van der Waals interaction with BM4 (PDB entry 4E92) (Lemke et al., 2012). Hence, the resistance mechanism of BM4 does not seem to operate through direct interactions. The crystal structures of BD-3 and BM4 bound to CA-NTD showed that both compounds are within interacting distance of M66, similar to CAP-1. Hence, BD and BM series compounds do not share a binding site with GS-CA1, but they all have a common interaction with M66.

Coumermycin A1 Binding to CA-Hexamers

Coumermycin A1 (C-A1) is a gyrase B inhibitor that also inhibits HSP90 (Vozzolo et al., 2010; reviewed in Carnes et al., 2018). A crystal structure of CA/C-A1 has not been solved. However, docking studies predict the binding of C-A1 in a pocket formed by two adjacent capsid monomers (Chen et al., 2016). This predicted binding site may be relevant, as mutations N74D and A105S conferred resistance to C-A1, and both residues (N74 and A105) are at the interface of two capsid monomers.

IFD was used to assess the details of interactions between C-A1 and CA. Of 32 predicted docking poses of C-A1 in the same PDB file (4XZF) as used by Chen et al., 2016, none of the poses were within interacting distance of N74 or A105. Docking data predict that that resistance of N74D and A105S to C-A1 may not be due to binding defects imparted by mutations at these residues.

Other Small Molecule Inhibitors of CA and their Comparison with the Binding of GS-CA1

Several additional CA inhibitors have been reported, such as CK026, I-XW-035 compound 34 (Kortagere et al., 2012), C1 (Lemke et al., 2013), and Ebselen (Lemke et al., 2013). CK026 is a large molecule, and was not shown to inhibit HIV-1 in PBMCs. However, I-XW-053 and compound 34, derivatives of CK026, demonstrated inhibitory activities in PBMCs (Kortagere et al., 2014). A crystal structure of CA in complex with these compounds has not been solved. However, the docking results in combination with binding affinity determination via surface plasmon resonance revealed that compound 34 binds in the vicinity of P38, S41, R173, K170, and Q179 (Kortagere et al., 2014). All of these residues are within interacting distance of GS-CA1 in the modeled CA/GS-CA1 complex (FIG. 2).

Compound C1 has been shown to bind at a unique site near the CypA-binding loop and affects late steps by disrupting proper assembly of mature capsid (Lemke et al., 2013). However, the crystal structures of CA in the presence of compound C1 and BD series compounds shows that C1 induces CA dimer formation and binds at the interface of the dimer. Mutation R132T confers resistance to C1. In the crystal structures of C1 and BD/BM compounds, R132 forms a polar interaction with compound C1. These structures also show that C1 makes contact with the N-terminus of helix 2, forming hydrophobic interactions with P34, G35, 137 and P38. The benzoic acid moiety forms a direct hydrogen bond to A139, and there is a water-mediated hydrogen bond to S41 (Lemke et al., 2013). Both 137 and P38 form hydrophobic interactions with GS-CA1 (FIG. 2).

Ebselen is a small molecule that was discovered in a search for inhibitors of CA dimerization. Electrospray ionization mass spectrometry experiments revealed that ebselen covalently binds CA-CTD, most likely through a selenylsulfide linkage involving C198 and C218 (Thenin-Houssier et al, 21016). Both of these residues are part of the CA-CTD, and they are not within interacting distance of the GS-CA1 in our modeled CA/GS-CA1 complex. Therefore, it is predicted that ebselen and GS-CA1 binding sites do not overlap.

Docking of a Designed Cyclic Peptide Inhibitor (Pep-2-Cyclic)

Using the crystal structures of PF74, NUP153, CPSF6, and BI-2-bound CA as well as the modeled structure of the CA/GS-CA1 (CA/GS-6207) complex, a cyclic peptide was designed (Pep-2-cyclic: Cyc(SGVFTFGPVNFPG); SEQ ID NO: 4) containing common structural components/groups among CA-bound small molecules or peptides derived from CPSF6 and NUP153. The docking of Pep-2-cyclic showed that it binds in a pocket that is shared by PF74, NUP153, CPSF6, GS-CA1 and GS-6207. The structural components that superposed in different complexes are listed in Table 1.

TABLE 1

Common structural groups/components in different CA complexes.

| PF74 | BI-2 | CPSF6 | NUP153 | GS-CA1 | Pep-2-cyclic |
|---|---|---|---|---|---|
| phenyl | phenyl | F321 | F1417 | difluorobenzyl | phenylalanine |
| phenyl | phenol | — | — | Indazole | proline |
| indole | — | G318-Q319[1] | — | cyclopenta-pyrazole | valine |
| — | — | | F1415 | methylsulfonyl | phenylalanine |

[1]A part of G318-Q319 is topologically close to the indole ring of PF74.

It appears that the designed peptide shares binding site and chemical moieties that may inhibit CA function.

Binding Affinity of CA with Pep-2-Cyclic and PF74

Pep-2-cyclic was synthesized chemically. Intermediate linear scaffolds were prepared by solid phase synthesis using a Fmoc/tbu strategy and starting with the very acid labile 2-ClTrt resin. After linear sequence assembly the fully protected peptide was removed from the resin by treatment with a mixture of 1% of TFA and 5% of TIS. Subsequently the peptide was cyclized by coupling the C-terminal carboxylic acid and the N-terminal amino group. This reaction was accomplished using PyBOP (2.5 excess) in presence of DIPEA (6× excess) in DMF solution for 6 hours at room temperature. After proofing cyclizations by 1c-ms, the other protecting groups were removed to obtain the final crude target molecules, by treating the protected cyclized intermediates with a mixture of TFA, and scavengers. Preparative HPLC purification and lyophilization yielded the final purified peptide which was characterized by 1c-ms.

MicroScale Thermophoresis (MST) assay was used to determine the binding affinity of CA to Pep-2-cyclic and PF74. MST is based on the thermophoresis, a directed movement of molecules in a temperature gradient, which depends on a variety of molecular properties including size, charge, hydration shell or conformation. Thus, it is highly sensitive to virtually any change in molecular properties, allowing for precise quantification of molecular events independent of the size or nature of the investigated sample (Jerabek-Willemsen, 2014). During the MST experiment, a temperature gradient is induced by an infrared laser. The directed movement of molecules through the temperature gradient is detected and quantified using covalently attached fluorophore. The binding isotherms obtained by plotting the difference in normalized fluorescence against increasing Pep-2-cyclic and PF74 concentration are shown in FIG. 6A and FIG. 6B, respectively. The binding affinities of Pep-2-cyclic ($K_{d,Pep\text{-}2\text{-}cyclic}$) and PF74 ($K_{d,PF74}$) with CA were extrapolated by fitting the data points to a quadratic equation (Equation 1). The $K_{d,Pep\text{-}2\text{-}cyclic}$ from these data is 32±3 nM, whereas the $K_{d,PF74}$ is 212±7 nM. The binding affinity of CA-hexamers with PF74 was previously determined by isothermal calorimetry (ITC) to be 262 nM (Bhattacharya et al., 2014), which is in good agreement with the $K_{d,PF74}$ determined here using MST. These data suggest that Pep-2-cyclic binds CA with ~7-fold greater affinity.

Cyclic Peptides

Thus, certain aspects of this disclosure are drawn to a cyclic peptide comprising the amino acid sequence of F-$X^1$-F-$X^2$-P-V-$X^3$-F (SEQ ID NO: 2), wherein $X^1$, $X^2$, and $X^3$ are each independently glycine (G), lysine (K), or a polar uncharged amino acid. In certain aspects of SEQ ID NO: 2:

$X^2$ is glycine and $X^1$ and $X^3$ are each a polar uncharged amino acid; and/or $X^1$ is threonine (T) and/or $X^3$ is asparagine (R).

In certain aspects of a cyclic peptide of this disclosure, the cyclic peptide comprises the amino acid sequence of $X^4$-$X^5$-$X^6$-F-$X^1$-F-$X^2$-P-V-$X^3$-F-$X^7$-$X^8$ (SEQ ID NO: 3), wherein the sequence F-$X^1$-F-$X^2$-P-V-$X^3$-F (SEQ ID NO: 2) is as defined above, and wherein $X^4$, $X^5$, $X^6$, $X^7$, and $X^8$ are each independently selected from the group consisting of glycine (G), proline (P), lysine (K), a polar uncharged amino acid, and a hydrophobic amino acid. In certain aspects of SEQ ID NO: 3:

$X^4$ is a polar uncharged amino acid;

$X^4$ is serine (S);

$X^6$ is a hydrophobic amino acid;

$X^6$ is valine (V);

$X^7$ is proline (P); and/or $X^5$ and/or $X^8$ are glycine (G).

In certain aspects of SEQ ID NO: 2 and/or SEQ ID NO: 3, at least one of $X^1$, $X^2$, $X^3$, $X^4$, $X^5$, $X^6$, $X^7$, or $X^8$ is lysine (K).

In certain aspects, a cyclic peptide of this disclosure comprises the amino acid sequence of S-G-V-F-T-F-G-P-V-N-F-P-G (SEQ ID NO: 4). In certain aspects, a cyclic peptide of this disclosure consists of the amino acid sequence of S-G-V-F-T-F-G-P-V-N-F-P-G (SEQ ID NO: 4). In certain aspects, a cyclic peptide of this disclosure comprises the amino acid sequence of S-G-V-F-Y-F-W-P-V-N-F-P-G (SEQ ID NO: 5). In certain aspects, a cyclic peptide of this disclosure consists of the amino acid sequence of S-G-V-F-Y-F-W-P-V-N-F-P-G (SEQ ID NO: 5).

In certain aspects, a cyclic peptide comprising SEQ ID NO: 2, SEQ ID NO: 3, SEQ ID NO: 4 and/or SEQ ID NO: 5 further comprises one or more additional amino acids. In certain aspects, at least one of the additional amino acids is lysine (K).

Certain aspects are drawn to a cyclic peptide comprising an amino acid sequence of S-G-V-F-T-F-G-P-V-N-F-P-G (SEQ ID NO: 4) or S-G-V-F-Y-F-W-P-V-N-F-P-G (SEQ ID NO: 5), except wherein the sequence has one or two changes selected from an amino acid substitution, a single amino acid addition; a single amino acid deletion, or a combination of two thereof. Certain aspects are drawn to a cyclic peptide consisting of the amino acid sequence of S-G-V-F-T-F-G-P-V-N-F-P-G (SEQ ID NO: 4) or S-G-V-F-Y-F-W-P-V-N-F-P-G (SEQ ID NO: 5), except wherein the sequence has one or two changes selected from an amino acid substitution, a single amino acid addition; a single amino acid deletion, or a combination of two thereof. That is, there could be up to two single amino acid additions, two single amino acid additions, or two single amino acid deletions, as long as the number of changes does not exceed two. That is, there could be one or any combination of a single amino substitution, a single amino acid addition, and a single amino acid deletion, as long as the number of changes does not exceed two. In certain aspects, the sequence has one or two amino acid substitutions but not an amino acid addition or amino acid deletion. In certain aspects, the sequence has only one amino acid substitution. And, in certain aspects, the amino acid substitution is a conservative amino acid substitution as recognized in the art. In certain aspects, such a cyclic peptide further comprises one or more additional amino acids. In certain aspects, at least one of the additional amino acids is lysine (K).

In certain aspects of any of the cyclic peptides disclosed herein, the cyclic peptide has a length of 50 amino acids or fewer, 40 amino acids or fewer, 30 amino acids or fewer, 25 amino acids or fewer, 20 amino acids or fewer, 19 amino acids or fewer, 18 amino acids or fewer, 17 amino acids or fewer, 16 amino acids or fewer, 15 amino acids or fewer, 14 amino acids or fewer, 13 amino acids or fewer, 12 amino acids or fewer, 11 amino acids or fewer, 10 amino acids or fewer, 9 amino acids or fewer, or has a length of 8 amino acids. In certain aspects of any of the cyclic peptides disclosed herein, the cyclic peptide has a length of 50 amino acids or fewer but not less than 8, 40 amino acids or fewer but not less than 8, 30 amino acids or fewer but not less than 8, 25 amino acids or fewer but not less than 8, 20 amino acids or fewer but not less than 8, 19 amino acids or fewer but not less than 8, 18 amino acids or fewer but not less than 8, 17 amino acids or fewer but not less than 8, 16 amino acids or fewer but not less than 8, 15 amino acids or fewer but not less than 8, 14 amino acids or fewer but not less than 8, 13 amino acids or fewer but not less than 8, 12 amino acids or fewer but not less than 8, 11 amino acids or fewer but not less than 8, 10 amino acids or fewer but not less than 8, 9 amino acids or fewer but not less than 8, or has a length of 8 amino acids.

In certain aspects, a cyclic peptide of this disclosure further comprises a dye, a chelator, a radionuclide, or any combination of a dye, a chelator, and a radionuclide, for example for in vitro or in vivo imaging and/or therapeutic purposes. Illustrative examples of dyes include, but are not limited to, fluorescein, tetramethylrhodamine, and near IR dyes (e.g., Alexafluor and Cy series, e.g., Cy5, Cy5.5, and Cy7). Illustrative examples of chelators include, but are not limited to, DOTA, NOTA, DFO, and TCMC. Illustrative examples of radionuclides include, but are not limited to $^{18}$F, $^{111}$In, $^{99}$mTc, $^{64}$Cu, $^{89}$Zr, $^{177}$Lu, $^{225}$Ac, $^{212}$Pb, and $^{203}$Pb.

In certain aspects, a cyclic peptide of this disclosure binds to an HIV-1 capsid protein. In certain aspects, the HIV-1 capsid protein has an amino acid sequence comprising:

```
                                        (SEQ ID NO: 1)
PIVQNLQGQMVHQAISPRTLNAWVKVIEEKAFSPEVIPMFTALSEGATPQ

DLNTMLNTVGGHQAAMQMLKDTINEEAAEWDRLHPVHAGPIAPGQMREPR

GSDIAGTTSTLQEQIAWMTSNPPIPVGDIYKRWIILGLNKIVRMYSPVSI

LDIKQGPKEPFRDYVDRFFKTLRAEQATQDVKNWMTDTLLVQNANPDCKT

ILRALGPGATLEEMTACQGVGGPSHKARVL
```

In certain aspects, the HIV-1 capsid protein has an amino acid comprising a sequence that is at least 85%, 90%, 95%, 97%, 98%, or 99% identical to SEQ ID NO: 1. In certain aspects, the HIV-1 capsid protein has an amino acid comprising a sequence that is at least 85%, 90%, 95%, 97%, 98%, or 99% identical to SEQ ID NO: 1 wherein the binding pocket is conserved with SEQ ID NO: 1.

In certain aspects, the cyclic peptide binds to a binding pocket of the HIV-1 capsid protein located between the C-terminus domain (CTD) and the N-terminus domain (NTD) of the capsid protein. In certain aspects, the cyclic peptide interacts with a residue of the HIV-1 capsid protein comprising L56 of SEQ ID NO: 1, N57 of SEQ ID NO: 1, M66 of SEQ ID NO: 1, or a combination of any thereof.

In certain aspects, a cyclic peptide of this disclosure has a binding affinity (see Examples) for the HIV-1 capsid protein that is higher in comparison to the well-characterized capsid inhibitor PF74. For example, in certain aspects, the binding affinity for the HIV-1 capsid protein of a cyclic peptide of this disclosure is at least about 2-fold higher, at least about 3-fold higher, at least about 4-fold higher, at least about 5-fold higher, at least about 6-fold higher, at least about 7-fold higher, at least about 8-fold higher, at least about 9-fold higher, or at least about 10-fold higher than the capsid inhibitor PF74.

In certain aspects, a cyclic peptide of this disclosure inhibits an HIV-1 capsid from assembling and/or disassembling as described elsewhere herein. In certain embodiment, the cyclic peptide has an $IC_{50}$ for inhibiting an HIV-1 capsid from assembling and/or disassembling of about 2 μM to about 4 μM. In certain embodiment, the cyclic peptide has an $IC_{50}$ for inhibiting an HIV-1 capsid from assembling and/or disassembling of about 3.2 μM.

In certain aspects, a cyclic peptide of this disclosure shows inhibitory activity.

Certain aspects provide for a method of producing a cyclic peptide of this disclosure. In certain aspects, the method comprises producing a linear peptide of the sequence desired for the cyclic peptide and cyclizing the linear peptide to produce the cyclic peptide. In certain aspects, the linear peptide is chemically synthesized, such as but not limited to the synthesis described elsewhere herein. In certain aspects, the linear peptide is translated in a host cell, such as using the isolated polynucleotides, vectors, and/or host cells described elsewhere herein.

Linear Peptides

Certain aspects of this disclosure are drawn to a linear peptide such as for use as a precursor to the a cyclic peptide of this disclosure or as an inhibitor itself. Thus, certain aspects of this disclosure are drawn to a linear peptide comprising the amino acid sequence of F-V-F-$X^2$-P-V-$X^3$-F (SEQ ID NO: 2), wherein $X^1$, $X^2$, and $X^3$ are each independently glycine (G), lysine (K), or a polar uncharged amino acid. In certain aspects of SEQ ID NO: 2:

$X^2$ is glycine and $X^1$ and $X^3$ are each a polar uncharged amino acid; and/or $X^1$ is threonine (T) and/or $X^3$ is asparagine (R).

In certain aspects of a linear peptide of this disclosure, the linear peptide comprises the amino acid sequence of $X^4$-$X^5$-$X^6$-F-$X^1$-F-$X^2$-P-V-$X^3$-F-$X^7$-$X^8$ (SEQ ID NO: 3), wherein the sequence F-$X^1$-F-$X^2$-P-V-$X^3$-F (SEQ ID NO: 2) is as defined above, and wherein $X^4$, $X^5$, $X^6$, $X^7$, and $X^8$ are each independently selected from the group consisting of glycine (G), proline (P), lysine (K), a polar uncharged amino acid, and a hydrophobic amino acid. In certain aspects of SEQ ID NO: 3:

$X^4$ is a polar uncharged amino acid;

$X^4$ is serine (S);

$X^6$ is a hydrophobic amino acid;

$X^6$ is valine (V);

$X^7$ is proline (P); and/or $X^5$ and/or $X^8$ are glycine (G).

In certain aspects of SEQ ID NO: 2 and/or SEQ ID NO: 3, at least one of $X^1$, $X^2$, $X^3$, $X^4$, $X^5$, $X^6$, $X^7$, or $X^8$ is lysine (K).

In certain aspects, a linear peptide of this disclosure comprises the amino acid sequence of S-G-V-F-T-F-G-P-V-N-F-P-G (SEQ ID NO: 4). In certain aspects, a linear peptide of this disclosure consists of the amino acid sequence of S-G-V-F-T-F-G-P-V-N-F-P-G (SEQ ID NO: 4). In certain aspects, a linear peptide of this disclosure comprises the amino acid sequence of S-G-V-F-Y-F-W-P-V-N-F-P-G (SEQ ID NO: 5). In certain aspects, a linear peptide of this disclosure consists of the amino acid sequence of S-G-V-F-Y-F-W-P-V-N-F-P-G (SEQ ID NO: 5).

In certain aspects, a linear peptide comprising SEQ ID NO: 2, SEQ ID NO: 3, and/or SEQ ID NO: 4 further comprises one or more additional amino acids. In certain aspects, at least one of the additional amino acids is lysine (K).

Certain aspects are drawn to a linear peptide comprising an amino acid sequence of S-G-V-F-T-F-G-P-V-N-F-P-G (SEQ ID NO: 4) or S-G-V-F-Y-F-W-P-V-N-F-P-G (SEQ ID NO: 5), except wherein the sequence has one or two changes selected from an amino acid substitution, a single amino acid addition; a single amino acid deletion, or a combination of two thereof. Certain aspects are drawn to a linear peptide consisting of the amino acid sequence of S-G-V-F-T-F-G-P-V-N-F-P-G (SEQ ID NO: 4) or S-G-V-F-Y-F-W-P-V-N-F-P-G (SEQ ID NO: 5), except wherein the sequence has one or two changes selected from an amino acid substitution, a single amino acid addition; a single amino acid deletion, or a combination of two thereof. That is, there could be up to two single amino acid additions, two single amino acid additions, or two single amino acid deletions, as long as the number of changes does not exceed two. That is, there could be one or any combination of a single amino substitution, a single amino acid addition, and a single amino acid deletion, as long as the number of changes does not exceed two. In certain aspects, the sequence has one or two amino acid substitutions but not an amino acid addition or amino acid deletion. In certain aspects, the sequence has only one amino acid substitution. And, in certain aspects, the amino acid substitution is a conservative amino acid substitution as recognized in the art. In certain aspects, such a linear peptide further comprises one or more additional amino acids. In certain aspects, at least one of the additional amino acids is lysine (K).

In certain aspects of any of the linear peptides disclosed herein, the linear peptide has a length of 50 amino acids or fewer, 40 amino acids or fewer, 30 amino acids or fewer, 25 amino acids or fewer, 20 amino acids or fewer, 19 amino acids or fewer, 18 amino acids or fewer, 17 amino acids or fewer, 16 amino acids or fewer, 15 amino acids or fewer, 14 amino acids or fewer, 13 amino acids or fewer, 12 amino acids or fewer, 11 amino acids or fewer, 10 amino acids or fewer, 9 amino acids or fewer, or has a length of 8 amino acids. In certain aspects of any of the linear peptides disclosed herein, the linear peptide has a length of 50 amino acids or fewer but not less than 8, 40 amino acids or fewer but not less than 8, 30 amino acids or fewer but not less than 8, 25 amino acids or fewer but not less than 8, 20 amino acids or fewer but not less than 8, 19 amino acids or fewer but not less than 8, 18 amino acids or fewer but not less than 8, 17 amino acids or fewer but not less than 8, 16 amino acids or fewer but not less than 8, 15 amino acids or fewer but not less than 8, 14 amino acids or fewer but not less than 8, 13 amino acids or fewer but not less than 8, 12 amino acids or fewer but not less than 8, 11 amino acids or fewer but not less than 8, 10 amino acids or fewer but not less than 8, 9 amino acids or fewer but not less than 8, or has a length of 8 amino acids.

In certain aspects, the linear peptide comprises a C-terminal acid. In certain aspects, the linear peptide comprises a C-terminal amide.

In certain aspects, a linear peptide of this disclosure further comprises a dye, a chelator, a radionuclide, or any combination of a dye, a chelator, and a radionuclide, for example for in vitro or in vivo imaging and/or therapeutic purposes. Illustrative examples of dyes include, but are not limited to, fluorescein, tetramethylrhodamine, and near IR dyes (e.g., Alexafluor and Cy series, e.g., Cy5, Cy5.5, and Cy7). Illustrative examples of chelators include, but are not limited to, DOTA, NOTA, DFO, and TCMC. Illustrative examples of radionuclides include, but are not limited to $^{18}$F, $^{111}$In, $^{99}$mTc, $^{64}$Cu, $^{89}$Zr, $^{177}$Lu, $^{225}$Ac, $^{212}$Pb, and $^{203}$Pb.

In certain aspects, a linear peptide of this disclosure binds to an HIV-1 capsid protein. In certain aspects, the HIV-1 capsid protein has an amino acid sequence comprising:

```
                                   (SEQ ID NO: 1)
PIVQNLQGQMVHQAISPRTLNAWVKVIEEKAFSPEVIPMFTALSEGATPQ

DLNTMLNTVGGHQAAMQMLKDTINEEAAEWDRLHPVHAGPIAPGQMREPR

GSDIAGTTSTLQEQIAWMTSNPPIPVGDIYKRWIILGLNKIVRMYSPVSI

LDIKQGPKEPFRDYVDRFFKTLRAEQATQDVKNWMTDTLLVQNANPDCKT

ILRALGPGATLEEMTACQGVGGPSHKARVL
```

19
20

In certain aspects, the HIV-1 capsid protein has an amino acid comprising a sequence that is at least 85%, 90%, 95%, 97%, 98%, or 99% identical to SEQ ID NO: 1. In certain aspects, the HIV-1 capsid protein has an amino acid comprising a sequence that is at least 85%, 90%, 95%, 97%, 98%, or 99% identical to SEQ ID NO: 1 wherein the binding pocket is conserved with SEQ ID NO: 1.

In certain aspects, the linear peptide binds to a binding pocket of the HIV-1 capsid protein located between the C-terminus domain (CTD) and the N-terminus domain (NTD) of the capsid protein. In certain aspects, the linear peptide interacts with a residue of the HIV-1 capsid protein comprising L56 of SEQ ID NO: 1, N57 of SEQ ID NO: 1, M66 of SEQ ID NO: 1, or a combination of any thereof.

In certain aspects, a linear peptide of this disclosure has a binding affinity (see Examples) for the HIV-1 capsid protein that is higher in comparison to the well-characterized capsid inhibitor PF74. For example, in certain aspects, the binding affinity for the HIV-1 capsid protein of a linear peptide of this disclosure is at least about 2-fold higher, at least about 3-fold higher, at least about 4-fold higher, at least about 5-fold higher, at least about 6-fold higher, at least about 7-fold higher, at least about 8-fold higher, at least about 9-fold higher, or at least about 10-fold higher than the capsid inhibitor PF74.

In certain aspects, a linear peptide of this disclosure inhibits an HIV-1 capsid from assembling and/or disassembling as described elsewhere herein. In certain embodiment, the linear peptide has an $IC_{50}$ for inhibiting an HIV-1 capsid from assembling and/or disassembling of about 2 μM to about 4 μM. In certain embodiment, the linear peptide has an $IC_{50}$ for inhibiting an HIV-1 capsid from assembling and/or disassembling of about 3.2 μM.

In certain aspects, a linear peptide of this disclosure shows inhibitory activity.

Certain aspects provide for a method of producing a linear peptide of this disclosure. In certain aspects, the linear peptide is chemically synthesized, such as but not limited to the synthesis described elsewhere herein. In certain aspects, the linear peptide is translated in a host cell, such as using the isolated polynucleotides, vectors, and/or host cells described elsewhere herein.

Certain aspects of this disclosure are drawn to a pharmaceutical composition comprising the cyclic or linear peptide described anywhere herein. In certain aspects, the pharmaceutical composition further comprise a pharmaceutically acceptable carrier. Certain aspects of this disclosure are drawn to a method of treating an HIV infection in a subject in need thereof. In certain aspects, the subject is a mammal. In certain aspects, the subject is a primate. In certain aspects, the subject is a human. In certain aspects, such method comprises administering a therapeutically effective amount of the pharmaceutical composition disclosed herein to the subject. Examples of methods of administering include, but are not limited to, intravenous, intraperitoneally, inhalation, orally, or topically.

Certain aspects of this disclosure are drawn to an isolated polynucleotide comprising a nucleic acid which encodes any of the peptide sequences described herein. In certain aspects, the polynucleotide further comprising a heterologous nucleic acid. In certain aspects, such a heterologous nucleic acid comprises a promoter operably associated with the nucleic acid encoding the therapeutic polypeptide. Certain aspects provide for a vector comprising a polynucleotide of this disclosure. In certain aspects, the vector is a plasmid, such as a pET24 plasmid. Certain aspects also provide for a host cell comprising a vector. In certain aspects, the host cell is a bacterium, an insect cell, a mammalian cell, or a plant cell. For example, in certain aspects, the host cell is the bacterium *Escherichia coli*.

EXAMPLES

Example 1

HIV-1 CA Structure Preparation

The X-ray crystal structure of native HIV-1 capsid protein bound to PF74 (PDB entry 4XZF) (Gres et al., 2015) was used to dock GS-CA1 and Coumermycin A1 (C-A1). Initial structures of GS-CA1 and C-A1 were generated with CHEMSKETCH (Advanced Chemistry Development, Inc., Toronto, Ontario, Canada). These structures were subsequently minimized using MACROMODEL followed by LIGPREP (Schrödinger Inc., NY). The PREPWIZARD (Schrödinger Inc., NY), which adds hydrogens, assigns bond orders, creates heteroatom states and samples conformations of water molecules, was used to prepare CA-hexamer for docking of GS-CA1 and C-A1.

Example 2

Docking of GS-CA1, GS-6207, and CA-1

All docking simulations were conducted by the Induced-Fit Docking (IFD) module of Schrödinger Suite (Schrödinger Inc., NY). The IFD used Glide (Schrödinger Inc., NY) and the Refinement module in Prime (Schrödinger Inc., NY) to accurately predict ligand binding modes and concomitant structural changes in the receptor. A grid of 36×36×36 Å centered on the PF74 in the crystal structure of the native form of CA-hexamer (PDB file 4XZF) for the docketing of GS-CA1, GS6207, and C-A1 was generated by the Receptor Grid Generation utility of Glide. The IFD optimized the side chain conformation to best determine the docking poses. The pose with the best IFD score was selected for comparison purposes.

Example 3

Docking of Designed Peptide Pep-2-Cyclic

The structure of peptide Pep-2-cyclic was generated by Prime and subjected to energy minimization using the MM/GBSA (molecular mechanics—generalized Born surface area) method Genheden and Ryde, 2010). The docking of the peptide into the crystal structure of CA-hexamer was conducted by IFD (Schrödinger Inc., NY). The best scoring complex of CA/Pep-2-cyclic peptide was selected for analysis. PATCHDOCK (Schneidman-Duhovny et al., 2005) was also used through the PatchDock web server on the world wide web at https://bioinfo3d.cs.tau.ac.il/PatchDock/ to assess if the two software predicted different docking confirmation of Pep-2-cyclic.

Example 4

MicroScale Thermophoresis (MST) Assays

Then binding affinities of CA with Pep-2-cyclic and PF74 were determined by measuring thermophoresis of fluorescently labeled CA-hexamers in the presence of increasing Pep-2-cyclic or PF74 concentrations. Peptide Pep-2-cyclic was synthesized in the Moleculare Interaction Core (University of Missouri) and PF74 was purchased from Sigma-Aldrich (St. Louis, MO, USA). Fluorescent labeling of CA with Alexa Fluor 647 analog NT647 was performed according to the manufacturer's instructions (MO-L004 Monolith Protein Labeling Kit; NanoTemper Technologies GmbH, Munich, Germany). 20 µM protein was incubated overnight with 3 molar excess of dye at room temperature in a conjugation buffer provided with the labeling kit. The unreacted dye was removed by filtration through a gravity flow column provided with the kit. The elution fractions were collected in 2×MST buffer (100 mM MOPS, pH 7.0, 200 mM NaCl, and 0.2% pluronic F-127). Fluorescence intensity of each fraction was evaluated by MST (Monolith NT.115, NanoTemper Technologies GmbH, Munich, Germany), and fractions containing labelled protein were pooled. Protein concentration was determined by NANODROP (Thermo Scientific, Waltham, MA) spectrophotometer. Aliquots were stored at −80° C. until use. The reaction mixtures containing 200 nM labeled CA and increasing concentrations of Pep-2-cyclic (1 nM to 2000 nM) were loaded in the capillaries and the thermophoresis was monitored at 20% LED power, high MST power with 20 seconds MST-on time. The data were analyzed using MO. Affinity software (version 2.3) (NanoTempet Technologies, CA) by fitting the data point to a quadratic equation (Equation 1) and plotting by PRISM (Version 6.0) (GraphPad Inc. La Jolla, CA).

$$F_{norm} = A \frac{(K_d + [CA_0] + [P_0]) - \sqrt{(K_d + [CA_0] + [P_0])^2 - 4[P_0][CA_0]}}{2[P_0]}$$ (Equation 1)

Where A is an arbitrary parameter, $K_d=[P][CA]/[P-CA]$, [P] is the concentration of free Pep-2-cyclic or PF74, [CA] is the concentration of free CA and $[CA_0]$ is the concentration of added CA and $P_0$ is the concentration of added Pep-2-cyclic or PF74.

The breadth and scope of the present disclosure should not be limited by any of the above-described exemplary embodiments, but should be defined only in accordance with the following paragraphs, claims, and their equivalents.

Paragraphs

1. A cyclic or linear peptide comprising the amino acid sequence of F-X¹-F-X²-P-V-X³-F (SEQ ID NO: 2), wherein X % X², and X³ are each independently glycine (G), lysine (K), or a polar uncharged amino acid.

2. The cyclic or linear peptide of paragraph 1, wherein X² is glycine and X¹ and X³ are each a polar uncharged amino acid.

3. The cyclic or linear peptide of paragraph 1 or 2, wherein X¹ is threonine (T) and/or X³ is asparagine (R).

4. The cyclic or linear peptide of any one of paragraphs 1 to 3, wherein the peptide comprises the amino acid sequence of X⁴-X⁵-X⁶-F-X¹-F-X²-P-V-X³-F-X⁷-X⁸ (SEQ ID NO: 3), and wherein X⁴, X⁵, X⁶, X⁷, and X⁸ are each independently selected from the group consisting of glycine (G), proline (P), lysine (K), a polar uncharged amino acid, and a hydrophobic amino acid.

5. The cyclic or linear peptide of paragraph 4, wherein X⁴ is a polar uncharged amino acid.

6. The cyclic or linear peptide of paragraph 4 or 5, wherein X⁴ is serine (S).

7. The cyclic or linear peptide of any one of paragraphs 4 to 6, wherein X⁶ is a hydrophobic amino acid.

8. The cyclic or linear peptide of any one of paragraphs 4 to 7, wherein X⁶ is valine (V).

9. The cyclic or linear peptide of any one of paragraphs 4 to 8, wherein X⁷ is proline (P).

10. The cyclic or linear peptide of any one of paragraphs 4 to 9, wherein X⁵ and/or X⁸ are glycine (G).

11. The cyclic or linear peptide of paragraph 1, wherein the peptide comprises or consists of the amino acid sequence S-G-V-F-T-F-G-P-V-N-F-P-G (SEQ ID NO: 4) or S-G-V-F-Y-F-W-P-V-N-F-P-G (SEQ ID NO: 5), optionally, wherein the peptide comprises or consists of the amino acid sequence S-G-V-F-T-F-G-P-V-N-F-P-G (SEQ ID NO: 4), optionally, wherein the peptide comprises or consists of the amino acid sequence S-G-V-F-Y-F-W-P-V-N-F-P-G (SEQ ID NO: 5).

12. The cyclic or linear peptide of any one of paragraphs 1 to 10, wherein at least one of X¹, X², X³, X⁴, X⁵, X⁶, X⁷, or X⁸ is lysine (K).

13. The cyclic or linear peptide of any one of paragraphs 1 to 12, wherein the peptide further comprises one or more additional amino acids, wherein at least one of the additional amino acids is lysine (K).

14. A cyclic or linear peptide comprising or consisting of an amino acid sequence of S-G-V-F-T-F-G-P-V-N-F-P-G (SEQ ID NO: 4) or S-G-V-F-Y-F-W-P-V-N-F-P-G (SEQ ID NO: 5), except wherein the sequence has one or two changes selected from an amino acid substitution, a single amino acid addition; a single amino acid deletion, or a combination of two thereof.

15. The cyclic or linear peptide of paragraph 14, wherein the sequence has one or two amino acid substitutions but not an amino acid addition or amino acid deletion.

16. The cyclic or linear peptide of paragraph 15, wherein the sequence has only one amino acid substitution.

17. The cyclic or linear peptide of any one of paragraphs 14 to 16, wherein the amino acid substitution is a conservative amino acid substitution.

18. The cyclic or linear peptide of any one of paragraphs 1 to 17, wherein the peptide further comprises a dye, a chelator, a radionuclide, or any combination of a dye, a chelator, and a radionuclide.

19. The cyclic or linear peptide of any one of paragraphs 1 to 18, wherein the peptide binds to an HIV-1 capsid protein.

20. The cyclic or linear peptide of paragraph 19, wherein the peptide binds to a binding pocket of the HIV-1 capsid protein located between the C-terminus domain (CTD) and the N-terminus domain (NTD) of the capsid protein.

21. The cyclic or linear peptide of paragraph 19 or 20, wherein the HIV-1 capsid protein has an amino acid sequence comprising:

```
                                    (SEQ ID NO: 1)
PIVQNLQGQMVHQAISPRTLNAWVKVIEEKAFSPEVIPMFTALSEGATPQ

DLNTMLNTVGGHQAAMQMLKDTINEEAAEWDRLHPVHAGPIAPGQMREPR

GSDIAGTTSTLQEQIAWMTSNPPIPVGDIYKRWIILGLNKIVRMYSPVSI

LDIKQGPKEPFRDYVDRFFKTLRAEQATQDVKNWMTDTLLVQNANPDCKT

ILRALGPGATLEEMTACQGVGGPSHKARVL
``` and the peptide interacts with a residue of the capsid protein comprising L56 of SEQ ID NO: 1, N57 of SEQ ID NO: 1, M66 of SEQ ID NO: 1, or a combination of any thereof.

22. The cyclic or linear peptide of any one of paragraphs 1 to 21, wherein the peptide has a length of 50 amino acids or fewer, 40 amino acids or fewer, 30 amino acids or fewer, 25 amino acids or fewer, 20 amino acids or fewer, 19 amino acids or fewer, 18 amino acids or fewer, 17 amino acids or fewer, 16 amino acids or fewer, 15 amino acids or fewer, 14 amino acids or fewer, 13 amino acids or fewer, 12 amino acids or fewer, 11 amino acids or fewer, 10 amino acids or fewer, 9 amino acids or fewer, or has a length of 8 amino acids.

23. The cyclic or linear peptide of any one of paragraphs 19 to 22, wherein the peptide has a binding affinity for the HIV-1 capsid protein that is at least about 2-fold higher, at least about 3-fold higher, at least about 4-fold higher, at least about 5-fold higher, at least about 6-fold higher, at least about 7-fold higher, at least about 8-fold higher, at least about 9-fold higher, or at least about 10-fold higher than capsid inhibitor PF74.

24. The cyclic or linear peptide of any one of paragraphs 1 to 23 wherein the peptide inhibits an HIV-1 capsid from assembling and/or disassembling.

25. The cyclic or linear peptide of paragraph 24 wherein the peptide has an $IC_{50}$ of about 2 µM to about 4 µM.

26. The cyclic or linear peptide of paragraph 25 wherein the peptide has an $IC_{50}$ of about 3.2 µM.

27. The peptide of any one of paragraphs 1 to 26, wherein the peptide is a linear peptide.

28. The peptide of any one of paragraphs 1 to 26, wherein the peptide is a cyclic peptide.

29. A method of producing the cyclic peptide of paragraph 28, the method comprising producing a linear peptide of the sequence desired for the cyclic peptide and cyclizing the linear peptide to produce the cyclic peptide, optionally wherein the linear peptide is chemically synthesized, or optionally wherein the linear peptide is translated in a host cell.

30. An isolated polynucleotide comprising a nucleic acid which encodes the peptide of any one of paragraphs 1 to 28.

31. The isolated polynucleotide of paragraph 30, further comprising a heterologous nucleic acid.

32. The isolated polynucleotide of paragraph 31, wherein said heterologous nucleic acid comprises a promoter operably associated with the nucleic acid encoding the peptide.

33. A vector comprising the polynucleotide of any one of paragraphs 30 to 32.

34. The vector of paragraph 33, wherein the vector is a plasmid.

35. A host cell comprising the vector of paragraph 33 or 34.

36. The host cell of paragraph 35, which is a bacterium, an insect cell, a mammalian cell or a plant cell.

37. A pharmaceutical composition comprising the peptide of any one of paragraphs 1 to 28 and a pharmaceutically acceptable carrier.

38. A method of treating an HIV infection in a subject in need thereof, the method comprising administering a therapeutically effective amount of the composition of paragraph 37 to the subject.

REFERENCES

ACD/ChemSketch (Freeware), version 2017.1.2, Advanced Chemistry Devlopment, INc. Toronto, ON, Canada, www.acdlabs.com, 2017.

Ambrose, Z., and Aiken, C. (2014). HIV-1 uncoating: connection to nuclear entry and regulation by host proteins. Virology 454-455, 371-379.

Antiretroviral Therapy Cohort, C. (2017). Survival of HIV-positive patients starting antiretroviral therapy between 1996 and 2013: a collaborative analysis of cohort studies. Lancet HIV 4, e349-e356.

Bhattacharya, A., Alam, S. L., Fricke, T., Zadrozny, K., Sedzicki, J., Taylor, A. B., Demeler, B., Pornillos, O., Ganser-Pornillos, B. K., Diaz-Griffero, F., Ivanov, D. N., and Yeager, M. (2014). Structural basis of HIV-1 capsid recognition by PF74 and CPSF6. Proc Natl Acad Sci USA 111, 18625-18630.

Blair, W. S., Pickford, C., Irving, S. L., Brown, D. G., Anderson, M., Bazin, R., Cao, J., Ciaramella, G., Isaacson, J., Jackson, L., Hunt, R., Kjerrstrom, A., Nieman, J. A., Patick, A. K., Perros, M., Scott, A. D., Whitby, K., Wu, H., and Butler, S. L. (2010). HIV capsid is a tractable target for small molecule therapeutic intervention. PLoS Pathog 6, e1001220.

Bocanegra, R., Rodriguez-Huete, A., Fuertes, M. A., Del Alamo, M., and Mateu, M. G. (2012). Molecular recognition in the human immunodeficiency virus capsid and antiviral design. Virus Res 169, 388-410.

Campbell, E. M., and Hope, T. J. (2015). HIV-1 capsid: the multifaceted key player in HIV-1 infection. Nat Rev Microbiol 13, 471-483.

Carnes, S. K., Sheehan, J. H., and Aiken, C. (2018). Inhibitors of the HIV-1 capsid, a target of opportunity. Curr Opin HIV AIDS 13, 359-365.

Chen, N. Y., Zhou, L., Gane, P. J., Opp, S., Ball, N. J., Nicastro, G., Zufferey, M., Buffone, C., Luban, J., Selwood, D., Diaz-Griffero, F., Taylor, I., and Fassati, A. (2016). HIV-1 capsid is involved in post-nuclear entry steps. Retrovirology 13, 28.

Curreli, F., Zhang, H., Zhang, X., Pyatkin, I., Victor, Z., Altieri, A., and Debnath, A. K. (2011). Virtual screening based identification of novel small-molecule inhibitors targeted to the HIV-1 capsid. Bioorg Med Chem 19, 77-90.

Fader, L. D., Bethell, R., Bonneau, P., Bos, M., Bousquet, Y., Cordingley, M. G., Coulombe, R., Deroy, P., Faucher, A. M., Gagnon, A., Goudreau, N., Grand-Maitre, C., Guse, I., Hucke, O., Kawai, S. H., Lacoste, J. E., Landry, S., Lemke, C. T., Malenfant, E., Mason, S., Morin, S., O'meara, J., Simoneau, B., Titolo, S., and Yoakim, C. (2011). Discovery of a 1,5-dihydrobenzo[b][1,4]diazepine-2,4-dione series of inhibitors of HIV-1 capsid assembly. Bioorg Med Chem Lett 21, 398-404.

Francis, A. C., and Melikyan, G. B. (2018). Single HIV-1 Imaging Reveals Progression of Infection through CA-Dependent Steps of Docking at the Nuclear Pore, Uncoating, and Nuclear Transport. Cell Host Microbe 23, 536-548 e536.

Gamble, T. R., Vajdos, F. F., Yoo, S., Worthylake, D. K., Houseweart, M., Sundquist, W. I., and Hill, C. P. (1996). Crystal structure of human cyclophilin A bound to the amino-terminal domain of HIV-1 capsid. Cell 87, 1285-1294.

Genheden, S., and Ryde, U. (2010). How to obtain statistically converged MM/GBSA results. J Comput Chem 31, 837-846.

Gres, A. T., Kirby, K. A., Kewalramani, V. N., Tanner, J. J., Pornillos, O., and Sarafianos, S. G. (2015). X-ray crystal structures of native HIV-1 capsid protein reveal conformational variability. Science 349, 99-103.

Harries, A. D., Suthar, A. B., Takarinda, K. C., Tweya, H., Kyaw, N. T., Tayler-Smith, K., and Zachariah, R. (2016). Ending the HIV/AIDS epidemic in low- and middle-income countries by 2030: is it possible? F1000Res 5, 2328.

Jarvis, L. M. (2017). Conquering HIV's capsid. Chem. Eng. News 95, 23-25.

Jerabek-Willemsen, M. T., T.; Wanner, R.; Roth, H. M.; Duhr, S.; Baaske, P.; Breitsprecher, D. (2014). MicroScale Thermophoresis: Interaction analysis and beyond. Journal of Molecular Structure 1077, 101-113.

Kelly, B. N., Kyere, S., Kinde, I., Tang, C., Howard, B. R., Robinson, H., Sundquist, W. I., Summers, M. F., and Hill, C. P. (2007). Structure of the antiviral assembly inhibitor CAP-1 complex with the HIV-1 CA protein. J Mol Biol 373, 355-366.

Kortagere, S., Madani, N., Mankowski, M. K., Schon, A., Zentner, I., Swaminathan, G., Princiotto, A., Anthony, K., Oza, A., Sierra, L. J., Passic, S. R., Wang, X., Jones, D. M., Stavale, E., Krebs, F. C., Martin-Garcia, J., Freire, E., Ptak, R. G., Sodroski, J., Cocklin, S., and Smith, A. B., 3rd (2012). Inhibiting early-stage events in HIV-1 replication by small-molecule targeting of the HIV-1 capsid. J Virol 86, 8472-8481.

Kortagere, S., Xu, J. P., Mankowski, M. K., Ptak, R. G., and Cocklin, S. (2014). Structure-activity relationships of a novel capsid targeted inhibitor of HIV-1 replication. J Chem Inf Model 54, 3080-3090.

Lamorte, L., Titolo, S., Lemke, C. T., Goudreau, N., Mercier, J. F., Wardrop, E., Shah, V. B., Von Schwedler, U. K., Langelier, C., Banik, S. S., Aiken, C., Sundquist, W. I., and Mason, S. W. (2013). Discovery of novel small-molecule HIV-1 replication inhibitors that stabilize capsid complexes. Antimicrob Agents Chemother 57, 4622-4631.

Lemke, C. T., Titolo, S., Goudreau, N., Faucher, A. M., Mason, S. W., and Bonneau, P. (2013). A novel inhibitor-binding site on the HIV-1 capsid N-terminal domain leads to improved crystallization via compound-mediated dimerization. Acta Crystallogr D Biol Crystallogr 69, 1115-1123.

Lemke, C. T., Titolo, S., Von Schwedler, U., Goudreau, N., Mercier, J. F., Wardrop, E., Faucher, A. M., Coulombe, R., Banik, S. S., Fader, L., Gagnon, A., Kawai, S. H., Rancourt, J., Tremblay, M., Yoakim, C., Simoneau, B., Archambault, J., Sundquist, W. I., and Mason, S. W. (2012). Distinct effects of two HIV-1 capsid assembly inhibitor families that bind the same site within the N-terminal domain of the viral CA protein. J Virol 86, 6643-6655.

Li, G., Verheyen, J., Rhee, S. Y., Voet, A., Vandamme, A. M., and Theys, K. (2013). Functional conservation of HIV-1 Gag: implications for rational drug design. Retrovirology 10, 126.

May, M. T., Gompels, M., Delpech, V., Porter, K., Orkin, C., Kegg, S., Hay, P., Johnson, M., Palfreeman, A., Gilson, R., Chadwick, D., Martin, F., Hill, T., Walsh, J., Post, F., Fisher, M., Ainsworth, J., Jose, S., Leen, C., Nelson, M., Anderson, J., Sabin, C., and Study, U.K.C.H.C. (2014). Impact on life expectancy of HIV-1 positive individuals of CD4+ cell count and viral load response to antiretroviral therapy. AIDS 28, 1193-1202.

Perrier, M., Bertine, M., Le Hingrat, Q., Joly, V., Visseaux, B., Collin, G., Landman, R., Yazdanpanah, Y., Descamps, D., and Charpentier, C. (2017). Prevalence of gag mutations associated with in vitro resistance to capsid inhibitor GS-CA1 in HIV-1 antiretroviral-naive patients. J Antimicrob Chemother 72, 2954-2955.

Pornillos, O., Ganser-Pornillos, B. K., Kelly, B. N., Hua, Y., Whitby, F. G., Stout, C. D., Sundquist, W. I., Hill, C. P., and Yeager, M. (2009). X-ray structures of the hexameric building block of the HIV capsid. Cell 137, 1282-1292.

Pornillos, O., Ganser-Pornillos, B. K., and Yeager, M. (2011). Atomic-level modelling of the HIV capsid. Nature 469, 424-427.

Prevelige, P. E., Jr. (2011). New approaches for antiviral targeting of HIV assembly. J Mol Biol 410, 634-640.

Price, A. J., Fletcher, A. J., Schaller, T., Elliott, T., Lee, K., Kewalramani, V. N., Chin, J. W., Towers, G. J., and James, L. C. (2012). CPSF6 defines a conserved capsid interface that modulates HIV-1 replication. PLoS Pathog 8, e1002896.

Price, A. J., Jacques, D. A., Mcewan, W. A., Fletcher, A. J., Essig, S., Chin, J. W., Halambage, U. D., Aiken, C., and James, L. C. (2014). Host cofactors and pharmacologic ligands share an essential interface in HIV-1 capsid that is lost upon disassembly. PLoS Pathog 10, e1004459.

Quinn, T. C. (2008). HIV epidemiology and the effects of antiviral therapy on long-term consequences. AIDS 22 Suppl 3, S7-12.

Sabin, C. A. (2013). Do people with HIV infection have a normal life expectancy in the era of combination antiretroviral therapy? BMC Med 11, 251.

Sager, J. E., Begley, R., Rhee, M., West, S. K., Ling, J., Schroeder, S. D., Tse, W. C., and Mathias, A. (2019). Safety and pK of subcutaneous GS-6207, a novel HIV-1 capsid inhibitor (Abstract #141). conference on Retroviruses and Opportunistic Infections, March 4-7, Seattle, WA, USA.

Schaller, T., Ocwieja, K. E., Rasaiyaah, J., Price, A. J., Brady, T. L., Roth, S. L., Hue, S., Fletcher, A. J., Lee, K., Kewalramani, V. N., Noursadeghi, M., Jenner, R. G., James, L. C., Bushman, F. D., and Towers, G. J. (2011). HIV-1 capsid-cyclophilin interactions determine nuclear import pathway, integration targeting and replication efficiency. PLoS Pathog 7, e1002439.

Schneidman-Duhovny, D., Inbar, Y., Nussinov, R., and Wolfson, H. J. (2005). PatchDock and SymmDock: servers for rigid and symmetric docking. Nucleic Acids Res 33, W363-367.

Shi, J., Zhou, J., Halambage, U. D., Shah, V. B., Burse, M. J., Wu, H., Blair, W. S., Butler, S. L., and Aiken, C. (2015). Compensatory substitutions in the HIV-1 capsid reduce the fitness cost associated with resistance to a capsid-targeting small-molecule inhibitor. J Virol 89, 208-219.

Shi, J., Zhou, J., Shah, V. B., Aiken, C., and Whitby, K. (2011). Small-molecule inhibition of human immunodeficiency virus type 1 infection by virus capsid destabilization. J Virol 85, 542-549.

Sticht, J., Humbert, M., Findlow, S., Bodem, J., Muller, B., Dietrich, U., Werner, J., and Krausslich, H. G. (2005). A peptide inhibitor of HIV-1 assembly in vitro. Nat Struct Mol Biol 12, 671-677.

Tang, C., Loeliger, E., Kinde, I., Kyere, S., Mayo, K., Barklis, E., Sun, Y., Huang, M., and Summers, M. F. (2003). Antiviral inhibition of the HIV-1 capsid protein. J Mol Biol 327, 1013-1020.

Teeraananchai, S., Kerr, S. J., Amin, J., Ruxrungtham, K., and Law, M. G. (2017). Life expectancy of HIV-positive people after starting combination antiretroviral therapy: a meta-analysis. HIV Med 18, 256-266.

Ternois, F., Sticht, J., Duquerroy, S., Krausslich, H. G., and Rey, F. A. (2005). The HIV-1 capsid protein C-terminal domain in complex with a virus assembly inhibitor. Nat Struct Mol Biol 12, 678-682.

Thenin-Houssier, S., De Vera, I. M., Pedro-Rosa, L., Brady, A., Richard, A., Konnick, B., Opp, S., Buffone, C., Fuhrmann, J., Kota, S., Billack, B., Pietka-Ottlik, M., Tellinghuisen, T., Choe, H., Spicer, T., Scampavia, L., Diaz-Griffero, F., Kojetin, D. J., and Valente, S. T. (2016). Ebselen, a Small-Molecule Capsid Inhibitor of HIV-1 Replication. Antimicrob Agents Chemother 60, 2195-2208.

27

28

Tremblay, M., Bonneau, P., Bousquet, Y., Deroy, P., Duan, J., Duplessis, M., Gagnon, A., Garneau, M., Goudreau, N., Guse, I., Hucke, O., Kawai, S. H., Lemke, C. T., Mason, S. W., Simoneau, B., Surprenant, S., Titolo, S., and Yoakim, C. (2012). Inhibition of HIV-1 capsid assembly: optimization of the antiviral potency by site selective modifications at N1, C2 and C16 of a 5-(5-furan-2-yl-pyrazol-1-yl)-1H-benzimidazole scaffold. Bioorg Med Chem Lett 22, 7512-7517.

Tse, W. C., Link, J. O., Mulato, A., Niedziela-Majka, A., Rowe, W., Somoza, J. R., Villasenor, A. G., Yant, S. R., Zhang, J. R., and Zheng, J. (2017). Discovery of Novel Potent HIV Capsid Inhibitors With Long-Acting Potential. Conference on Retroviruses and Opportunistic Infections Abstract No. 38, Feb. 13-16, 2017, Seattle, Washington.

Vozzolo, L., Loh, B., Gane, P. J., Tribak, M., Zhou, L., Anderson, I., Nyakatura, E., Jenner, R. G., Selwood, D., and Fassati, A. (2010). Gyrase B inhibitor impairs HIV-1 replication by targeting Hsp90 and the capsid protein. J Biol Chem 285, 39314-39328.

Zhang, H., Curreli, F., Waheed, A. A., Mercredi, P. Y., Mehta, M., Bhargava, P., Scacalossi, D., Tong, X., Lee, S., Cooper, A., Summers, M. F., Freed, E. O., and Debnath, A. K. (2013). Dual-acting stapled peptides target both HIV-1 entry and assembly. Retrovirology 10, 136.

Zheng, J., Yant, S. R., Ahmadyar, S., Chan, T. Y., Chiu, A., Cihlar, T., Link, J. O., Lu, B., Mwangi, J., Rowe, W., Schroeder, S. D., Stepan, G. J., Wang, K. W., Subramanian, R., and Tse, W. C. (2018). 539. GS-CA2: A Novel, Potent, and Selective First-In-class Inhibitor of HIV-1 Capsid Function Displays Nonclinical Pharmacokinetics Supporting Long-Acting Potential in Humans. Open Forum Infectious Diseases 5, S199-S200.

Zhou, J., Price, A. J., Halambage, U. D., James, L. C., and Aiken, C. (2015). HIV-1 Resistance to the Capsid-Targeting Inhibitor PF74 Results in Altered Dependence on Host Factors Required for Virus Nuclear Entry. J Virol 89, 9068-9079.

---

What is claimed is:

1. A cyclic peptide comprising the amino acid sequence of F-$X^1$-F-$X^2$-P-V-$X^3$-F (SEQ ID NO: 2), wherein $X^1$, $X^2$, and $X^3$ are each independently glycine (G), lysine (K), or a polar uncharged amino acid.

2. The cyclic peptide of claim 1, wherein $X^2$ is glycine (G) and $X^1$ and $X^3$ are each a polar uncharged amino acid.

3. The cyclic peptide of claim 2, wherein $X^1$ is threonine (T) and/or $X^3$ is asparagine (N).

4. The cyclic peptide of claim 1, wherein the peptide comprises the amino acid sequence of $X^4$-$X^5$-$X^6$-F-$X^1$-F-$X^2$-P-V-$X^3$-F-$X^7$-$X^8$ (SEQ ID NO: 3), and wherein $X^4$, $X^5$, $X^6$, $X^7$, and $X^8$ are each independently selected from the group consisting of glycine (G), proline (P), lysine (K), a polar uncharged amino acid, and a hydrophobic amino acid.

5. The cyclic peptide of claim 4, wherein $X^4$ is a polar uncharged amino acid.

6. The cyclic peptide of claim 5, wherein $X^4$ is serine(S).

7. The cyclic peptide of claim 4, wherein $X^6$ is a hydrophobic amino acid.

8. The cyclic peptide of claim 7, wherein $X^6$ is valine (V).

9. The cyclic peptide of claim 4, wherein $X^7$ is proline (P).

10. The cyclic peptide of claim 4, wherein $X^5$ and/or $X^8$ are glycine (G).

11. The cyclic peptide of claim 1, wherein the peptide comprises the amino acid sequence S-G-V-F-T-F-G-P-V-N-F-P-G (SEQ ID NO: 4) or S-G-V-F-Y-F-W-P-V-N-F-P-G (SEQ ID NO: 5).

12. The cyclic peptide of claim 1, wherein the peptide has a length of 50 amino acids or fewer.

13. A pharmaceutical composition comprising the peptide of claim 1 and a pharmaceutically acceptable carrier.

14. A cyclic or linear peptide comprising an amino acid sequence of S-G-V-F-T-F-G-P-V-N-F-P-G (SEQ ID NO: 4) or S-G-V-F-Y-F-W-P-V-N-F-P-G (SEQ ID NO: 5), or a cyclic peptide comprising an amino acid sequence of S-G-V-F-T-F-G-P-V-N-F-P-G (SEQ ID NO: 4) or S-G-V-F-Y-F-W-P-V-N-F-P-G (SEQ ID NO: 5) except wherein the sequence has one or two amino acid substitutions.

15. The cyclic or linear peptide of claim 14, wherein the sequence has only one amino acid substitution.

16. The cyclic or linear peptide of claim 14, wherein the one or two amino acid substitutions are conservative amino acid substitutions.

17. The cyclic or linear peptide of claim 14, wherein the peptide has a length of 50 amino acids or fewer.

18. The cyclic or linear peptide of claim 14, comprising an amino acid sequence of S-G-V-F-T-F-G-P-V-N-F-P-G (SEQ ID NO: 4), or an amino acid sequence of S-G-V-F-T-F-G-P-V-N-F-P-G (SEQ ID NO: 4) except wherein the sequence has one or two amino acid substitutions.

19. The cyclic or linear peptide of claim 14 comprising an amino acid sequence of S-G-V-F-T-F-G-P-V-N-F-P-G (SEQ ID NO: 4).

20. A pharmaceutical composition comprising the peptide of claim 14 and a pharmaceutically acceptable carrier.

21. An isolated polynucleotide comprising a nucleic acid which encodes the peptide of claim 1.

22. A vector comprising the polynucleotide of claim 21.

23. A host cell comprising the vector of claim 22.

24. A method of producing the cyclic peptide of claim 1, the method comprising producing a linear peptide of the sequence desired for the cyclic peptide and cyclizing the linear peptide to produce the cyclic peptide.

25. A method of treating an HIV infection in a subject in need thereof, the method comprising administering a therapeutically effective amount of a pharmaceutical composition comprising a cyclic peptide comprising an amino acid sequence of G-V-F-T-F-G-P-V-N-F-P-G (SEQ ID NO: 4) and a pharmaceutically acceptable carrier to the subject.

* * * * *